United States Patent
Or et al.

(10) Patent No.: US 7,589,067 B2
(45) Date of Patent: Sep. 15, 2009

(54) 6, 11-BRIDGED TRICYCLIC MACROLIDES

(75) Inventors: Yat Sun Or, Watertown, MA (US); Guoqiang Wang, Belmont, MA (US); Tongzhu Liu, Auburndale, MA (US); Ly Tam Phan, Quincy, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 332 days.

(21) Appl. No.: 11/545,241

(22) Filed: Oct. 10, 2006

(65) Prior Publication Data

US 2007/0082853 A1   Apr. 12, 2007

Related U.S. Application Data

(60) Provisional application No. 60/725,937, filed on Oct. 12, 2005.

(51) Int. Cl.
*A61K 31/70* (2006.01)
*C07H 17/08* (2006.01)

(52) U.S. Cl. .......................... 514/29; 536/7.4
(58) Field of Classification Search .................. 536/7.4
See application file for complete search history.

(56) References Cited

U.S. PATENT DOCUMENTS

| | | | |
|---|---|---|---|
| 6,046,171 | A | 4/2000 | Or et al. |
| 6,878,691 | B2 | 4/2005 | Or et al. |
| 7,064,110 | B2 | 6/2006 | Or et al. |
| 2005/0009761 | A1 | 1/2005 | Or et al. |
| 2005/0159370 | A1 | 7/2005 | Or et al. |
| 2005/0171033 | A1 | 8/2005 | Qiu et al. |

FOREIGN PATENT DOCUMENTS

| | | |
|---|---|---|
| WO | WO 99/21864 | 5/1999 |
| WO | WO 03/095466 A1 | 11/2003 |
| WO | WO 03/097659 A1 | 11/2003 |

*Primary Examiner*—Elli Peselev
(74) *Attorney, Agent, or Firm*—Carolyn S. Elmore; Edgar W. Harlan; Elmore Patent Law Group P.C.

(57) ABSTRACT

The present invention discloses compounds of formula I, or pharmaceutically acceptable salts, esters, or prodrugs thereof:

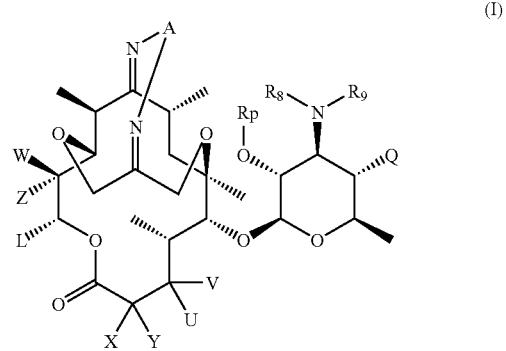

(I)

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

13 Claims, No Drawings

6,11-BRIDGED TRICYCLIC MACROLIDES

RELATED APPLICATION

This application claims the benefit of U.S. Provisional Application No. 60/725,937, filed on Oct. 12, 2005. The entire teachings of the above application are incorporated herein by reference.

TECHNICAL FIELD

The present invention relates to novel semisynthetic macrolides having antibacterial activity that are useful in the treatment and prevention of bacterial infections. More particularly, the invention relates to 6,11-bridged tricyclic erythromycin compounds, compositions containing such compounds and methods for using the same, as well as processes for making such compounds.

BACKGROUND OF THE INVENTION

The spectrum of activity of macrolides, including erythromycin, covers most relevant bacterial species responsible for upper and lower respiratory tract infections. 14-membered ring macrolides are well known for their overall efficacy, safety and lack of serious side effects. Erythromycin however is quickly degraded into inactive products in the acidic medium of the stomach resulting in low bioavailability and gastrointestinal side effects. Improvement of erythromycin pharmacokinetics has been achieved through the synthesis of more acid-stable derivatives, for example, roxithromycin, clarithromycin, and the 15-membered ring macrolide azithromycin.

However, all these drugs, including 16-membered ring macrolides, present several drawbacks. They are inactive against $MLS_B$-resistant streptococci ($MLS_B$=Macrolides-Lincosamides-type B Streptogramines) and with the exception of azithromycin, weakly active against *Haemophilus influenzae*. Furthermore, the resistance of *Streptococcus pneumoniae* to erythromycin has increased significantly in recent years (5% to above 40%). There is a high percentage of cross-resistance to penicillin among these isolates, with a worldwide epidemic spread of 10-40% in some areas.

There is, therefore, a clear need for new macrolides that overcome the problem of pneumococcal resistance, have good pharmacokinetic properties and acid stability while continuing to be active against *H. influenzae*. These new macrolides will be ideal candidates for drug development in the first line therapy of upper respiratory tract infections ("URTI") and lower respiratory tract infections ("LRTI").

Kashimura et al. have disclosed 6-O-methylerythromycin derivatives having a tricyclic basic nuclear structure in European Application 559896, published Nov. 11, 1991. Also, Asaka et al. have disclosed 5-O-desoaminylerythronolide derivatives containing a tricyclic carbamate structure in PCT Application WO 93/21200, published Apr. 22, 1992.

Recently erythromycin derivatives containing a variety of substituents at the 6-O-position have been disclosed in U.S. Pat. Nos. 5,866,549 and 6,075,011 as well as PCT Application WO00/78773. Furthermore, Ma et. al. have described erythromycin derivatives with aryl groups tethered to the C-6 position in *J Med. Chem.*, 44, pp 4137-4156 (2001). PCT application WO 97/10251, published Mar. 20, 1997, discloses intermediates useful for preparation of 6-O-methyl 3-descladinose erythromycin derivatives. U.S. Pat. Nos. 5,866,549 and 6,075,011, and PCT application WO 00/78773, published Dec. 28, 2000, disclose certain 6-O-substituted erythromycin derivatives.

PCT Application WO 03/095466 A1, published Nov. 20, 2003 and PCT Application WO 03/097659 A1, published Nov. 27, 2003 disclose a series of bridged bicyclic erythromycin derivatives.

U.S. Pat. No. 6,075,011, and PCT Application WO 03/068791 A2, published Aug. 21, 2003 disclose a series of C9, C11 and C12 modified erythromycin ketolides.

SUMMARY OF THE INVENTION

The present invention provides a novel class of 6,11-bridged tricyclic macrolides that possess antibacterial activity.

In one embodiment, the compounds of the present invention are represented by formula (I), as illustrated below:

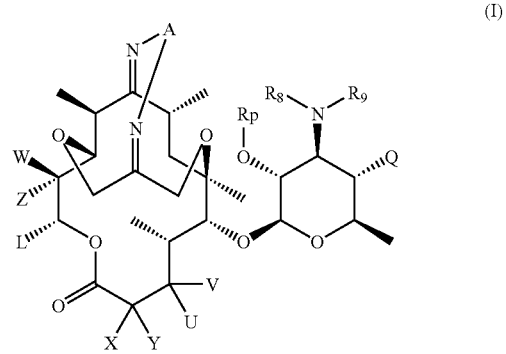

(I)

or the racemates, enantiomers, distereomers, geometric isomers, tautomers, solvates, pharmaceutically acceptable salts, esters and prodrugs thereof, wherein A is -J-$R_1$—, where J is absent or is selected from the group consisting of: O, OC(O), C(O), S(O)$_n$, NH, NH(CO), NH(CO)NH, or NHS(O)$_n$ where n is 0, 1, or 2 and $R_1$ is absent or is a substituted or unsubstituted —$C_1$-$C_8$ alkylene, —$C_2$-$C_8$ alkenylene or —$C_2$-$C_8$ alkynylene optionally containing one or more heteroatoms selected from O, S or N.

L is:

a) —$CH_2CH_3$;

b) —$CH(OH)CH_3$; or c) —$R_2$, where $R_2$ is:

i. —$C_1$-$C_6$ alkyl containing 0, 1, 2, or 3 heteroatoms selected from O, S or N, optionally substituted with one or more substituents selected from halogen, aryl, substituted aryl, heteroaryl, substituted heteroaryl; or ii. —$C_2$-$C_6$ alkenyl containing 0, 1, 2, or 3 heteroatoms selected from O, S or N, optionally substituted with one or more substituents selected from halogen, aryl, substituted aryl, heteroaryl, or substituted heteroaryl;

iii. —$C_1$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;

Q is:

a) hydrogen;

b) protected hydroxyl; or c) —OR$_3$, where R$_3$ is selected from the group consisting of:
  i. hydrogen;
  ii. aryl;
  iii. substituted aryl;
  iv. heteroaryl;
  v. substituted heteroaryl;
  vi. —R$_2$; or
  vii. C$_3$-C$_{12}$ cycloalkyl containing 0, 1, 2, or 3 heteroatoms selected from O, S or N, optionally substituted with one or more substituents selected from halogen, aryl, substituted aryl, heteroaryl, or substituted heteroaryl;

One U or V is hydrogen and the other is independently:
  a) hydrogen;
  b) hydroxyl;
  c) protected hydroxyl;
  d) —R$_2$;
  e) —OR$_2$;
  f) —C(O)R$_2$;
  g) —OC(O)R$_2$;
  h) —S(O)$_n$R$_2$; or
  i)

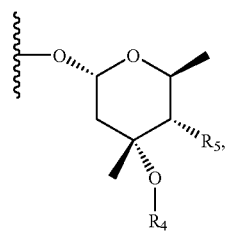

where R$_4$ is selected from the group consisting of hydrogen or/and methyl and R$_5$ is:
  i. hydrogen;
  ii. hydroxyl or hydroxyl protecting group;
  iii. —R$_2$; or
  iv. —OR$_2$;

Alternatively, U and V taken together with the carbon atom to which they are attached to form a carbonyl group;
W is:
  a) hydroxyl;
  b) —NR$_6$R$_7$, where each R$_6$ and R$_7$ are hydrogen or R$_2$ or R$_6$ and R$_7$ taken together with the nitrogen atom to which they are attached to form a substituted or unsubstituted heterocyclic ring.
  c) —O—R$_2$; or
  d) —OC(O)NR$_6$R$_7$.
Z is:
  a) hydrogen;
  b) —N$_3$;
  c) —CN;
  d) —NO$_2$;
  e) —CONH$_2$;
  f) —COOH;
  g) —CHO;
  h) —R$_2$;
  i) —COOR$_2$;
  j) —C(O)R$_2$; or
  k) —C(O)NR$_6$R$_7$.

Alternatively, W and Z taken together with the carbon to which they are attached to form an olefin, or substituted olefin, an epoxide, a carbonyl, substituted or unsubstituted heterocyclic ring, or a C$_3$-C$_7$ carbocyclic, carbonate, or carbamate;

Each of X and Y is independently:
  a) hydrogen;
  b) halogen; or
  c) —R$_2$;

Each of R$_8$ and R$_9$ is independently selected from the group R$_2$; or R$_8$ and R$_9$ can be taken together with the nitrogen atom to which they are attached to form a substituted or unsubstituted heterocyclic ring;

R$_p$ is hydrogen, hydroxyl protecting group or hydroxyl prodrug group.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections in a subject in need of such treatment with said pharmaceutical compositions. Suitable carriers and formulations of the compounds of the present invention are disclosed.

In a further aspect of the present invention there are provided processes for the preparation of any 6,11 bridged tricyclic erythromycin derivatives of formula (I) via any synthetic route delineated herein.

DETAILED DESCRIPTION OF THE INVENTION

In a first embodiment of the compounds of the present invention are compounds represented by formula (I) as illustrated above, or a pharmaceutically acceptable salt, ester or prodrug thereof.

In a second embodiment of the compounds of the present invention are compounds represented by formula (II) as illustrated below, or a pharmaceutically acceptable salt, ester or prodrug thereof:

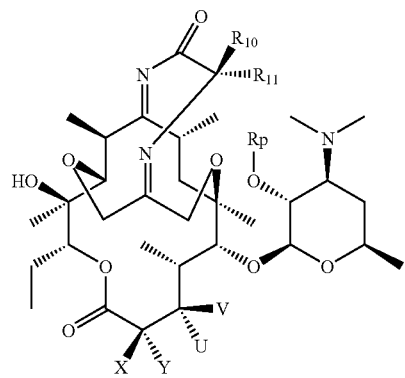

(II)

Each of R$_{10}$ and R$_{11}$ is independently:
  a) hydrogen;
  b) deuterium;
  c) halogen;
  d) —R$_2$;
  e) —COR$_2$;
  f) —SO$_2$R$_2$; or
  g) alternatively, can be taken together with the carbon atom to which they are attached are selected from the group consisting of: C=O and C=CHR$_2$;

In a third embodiment of the compounds of the present invention are compounds represented by formula (III) as illustrated below, or a pharmaceutically acceptable salt, ester or prodrug thereof:

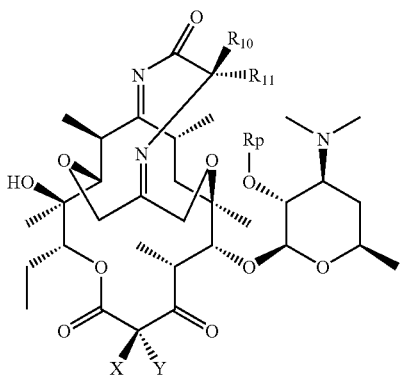

(III)

In a fourth embodiment of the compounds of the present invention are compounds represented by formula (IV) as illustrated below, or a pharmaceutically acceptable salt, ester or prodrug thereof:

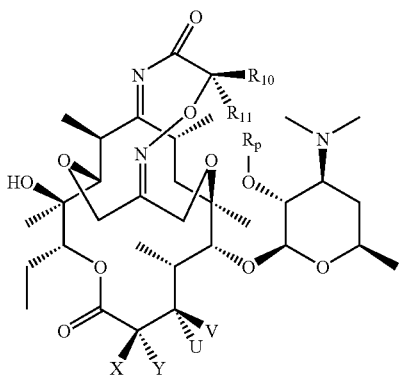

(IV)

In a fifth embodiment of the compounds of the present invention are compounds represented by formula (V) as illustrated below, or a pharmaceutically acceptable salt, ester or prodrug thereof:

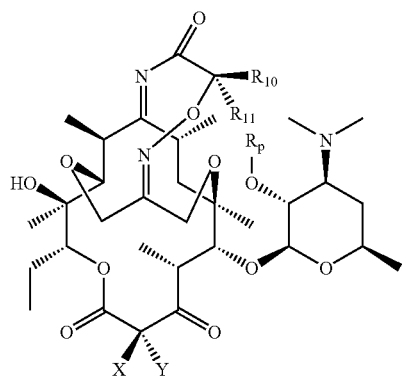

(V)

A compound according to any of formulas (I) to (V) invention selected from the group consisting of:

(1) Compound of formula (IV), wherein V, Y, $R_{10}$ and $R_{11}$ are hydrogen, X is methyl, $R_p$=Ac, and U is hydroxyl;
(2) Compound of formula (IV), wherein V, Y, and $R_{11}$ are hydrogen, $R_{10}$=Ph, X is methyl, $R_p$=Ac, and U is hydroxyl;
(3) Compound of formula (IV), wherein V, Y, and $R_{11}$ are hydrogen, $R_{10}$=Bn, X is methyl, $R_p$=Ac, and U is hydroxyl;
(4) Compound of formula (IV), wherein V, Y, and $R_{10}$ are hydrogen, $R_{11}$=Bn, X is methyl, $R_p$=Ac, and U is hydroxyl;
(5) Compound of formula (IV), wherein V, Y, and $R_{11}$ are hydrogen, $R_{10}$=CH$_2$CH$_2$Ph, X is methyl, $R_p$=Ac, and U is hydroxyl;
(6) Compound of formula (V), wherein Y, $R_{10}$ and $R_{11}$ are hydrogen, X is methyl, and $R_p$=H;
(7) Compound of formula (V), wherein Y, and $R_{11}$ are hydrogen, $R_{10}$=Ph, X is methyl, and $R_p$=H;
(8) Compound of formula (V), wherein Y, and $R_{11}$ are hydrogen, $R_{10}$=Bn, X is methyl, and $R_p$=H;
(9) Compound of formula (V), wherein Y, and $R_{10}$ are hydrogen, $R_{11}$=Bn, X is methyl, and $R_p$=H; and
(10) Compound of formula (V), wherein Y, and $R_{11}$ are hydrogen, $R_{10}$=CH$_2$CH$_2$Ph, X is methyl, and $R_p$=H.

Further representative species of the present invention are:
Compounds (11)-(107) of the formula (A):

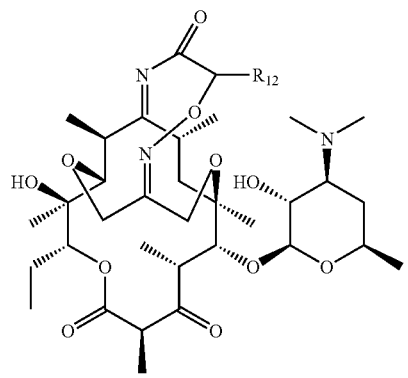

(A)

wherein $R_{12}$ is delineated for each example in Table 1.

TABLE 1

| Compound | $R_{12}$ |
|---|---|
| (11) | $_3$-) |
| (12) | |

TABLE 1-continued

| Compound | R₁₂ |
|---|---|
| (13) | 3-pyridylmethyl |
| (14) | 5-(2-pyridyl)thiophen-2-ylmethyl |
| (15) | quinolin-3-ylmethyl |
| (16) | (E)-4-phenylbut-3-enyl |
| (17) | (E)-3-phenylallyloxyethyl |
| (18) | (E)-3-(pyridin-2-yl)allyloxyethyl |
| (19) | (E)-3-(pyridin-3-yl)allyloxyethyl |
| (20) | (E)-3-(quinolin-3-yl)allyloxyethyl |
| (21) | (2-aminopyridin-4-yl)methyl |
| (22) | 2-(2-(pyridin-2-yl)ethylamino)ethyl |
| (23) | 2-(N-methyl-N-(2-(pyridin-2-yl)ethyl)amino)ethyl |
| (24) | 4-(pyridin-2-yl)but-3-ynyl |
| (25) | 4-(benzotriazol-1-yl)butyl |
| (26) | 4-(benzimidazol-1-yl)butyl |
| (27) | (E)-3-(5-carbamoylthiophen-2-yl)allyl |
| (28) | (E)-3-(3-carbamoylphenyl)allyl |
| (29) | 3-(6-chloropyridin-3-yl)propyl |

TABLE 1-continued

| Compound | R₁₂ |
|---|---|
| (30) | 4-carbamoylbenzyl group |
| (31) | 4-aminobenzyl group |
| (32) | 5-(pyridin-2-yl)-2,2'-bithiophen-5'-ylmethyl group |
| (33) | 6-(1H-pyrazol-1-yl)pyridin-3-ylmethyl group |
| (34) | 4-[5-(pyridin-2-yl)thiophen-2-yl]but-3-yn-1-yl group |
| (35) | 4-(quinolin-3-yl)but-3-yn-1-yl group |
| (36) | 4-(quinolin-3-yl)but-3-en-1-yl group |
| (37) | 4-(2-aminopyridin-3-yl)but-3-en-1-yl group |
| (38) | 3-(2-aminopyridin-3-yl)allyloxyethyl group |
| (39) | N-[3-(2-aminopyridin-3-yl)allyl]aminoethyl group |
| (40) | N-[2-(2-aminopyridin-3-yl)ethyl]aminopropyl group |
| (41) | 4-(6-aminopyridin-3-yl)but-3-en-1-yl group |
| (42) | 2-(6-amino-5-cyanopyridin-2-yl)ethyl group |
| (43) | 5-(pyridin-3-yl)thiophen-2-ylmethyl group |
| (44) | 5-(pyrazin-2-yl)thiophen-2-ylmethyl group |
| (45) | pyridin-4-ylmethyl group |

TABLE 1-continued

| Compound | R₁₂ |
|---|---|
| (46) | 3-phenylisoxazol-5-ylmethyl |
| (47) | 3-(1H-imidazol-2-yl)isoxazol-5-ylmethyl |
| (48) | 5-(pyrimidin-5-yl)thiophen-2-ylmethyl |
| (49) | 5-(pyrimidin-2-yl)thiophen-2-ylmethyl |
| (50) | isoquinolin-1-ylmethyl |
| (51) | 1H-benzimidazol-2-ylmethyl |
| (52) | 1-(pyrimidin-2-yl)-1H-pyrazol-3-ylmethyl |
| (53) | 3-(imidazo[4,5-b]pyridin-1-yl)propyl |
| (54) | 3-(9H-purin-9-yl)propyl |
| (55) | 1-benzyl-1H-imidazol-2-ylmethyl |
| (56) | 1-(5-(pyridin-2-yl)thiophen-2-yl)ethyl |
| (57) | 5-(thiophen-2-yl)-1,2,4-oxadiazol-3-ylmethyl |
| (58) | 5-carbamoylthiophen-2-ylmethyl |
| (59) | 3-(pyridin-2-yl)thiophen-2-ylmethyl |
| (60) | 5-(N-(pyridin-2-yl)carbamoyl)thiophen-2-ylmethyl |

TABLE 1-continued
| Compound | R₁₂ |
|---|---|
| (61) | 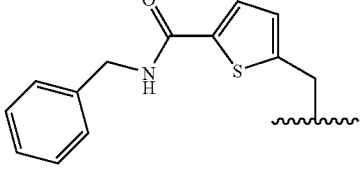 |
| (62) | 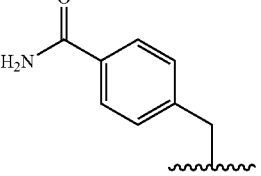 |
| (63) | 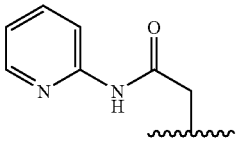 |
| (64) | 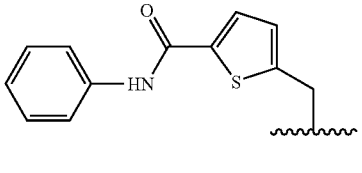 |
| (65) | 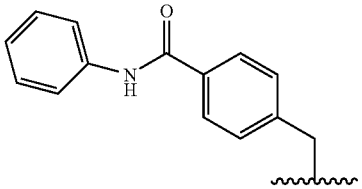 |
| (66) | 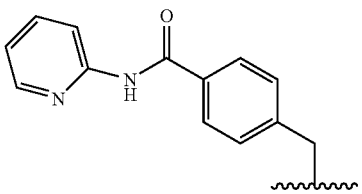 |
| (67) | 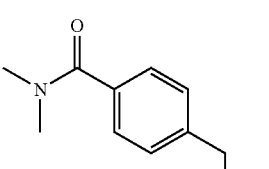 |
| (68) | 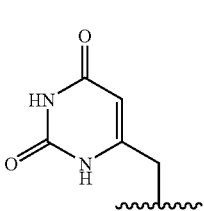 |
| (69) | 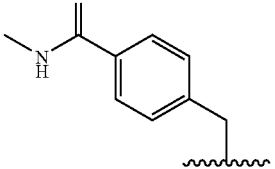 |
| (70) | 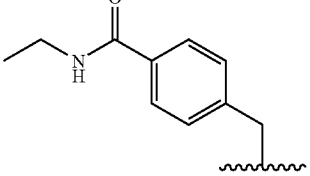 |
| (71) | 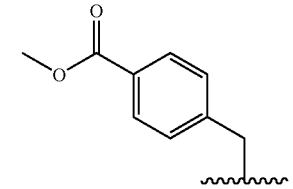 |
| (72) | 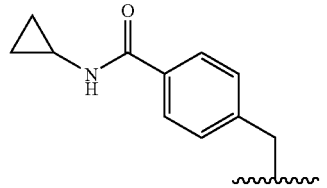 |
| (73) | 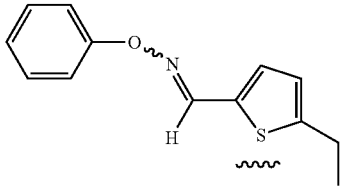 |
| (74) | 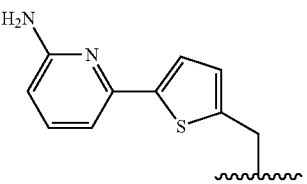 |
| (75) | 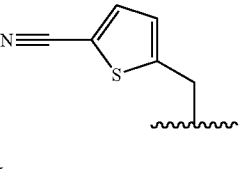 |
| (76) | 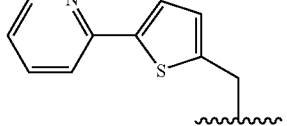 |

TABLE 1-continued

| Compound | R₁₂ |
|---|---|
| (77) | 6-(5-CH₂-isoxazol-3-yl)-pyridine-2-carbonitrile |
| (78) | 5-(thiophen-2-yl)pyridin-2-yl methylene (2-thienyl-pyridine with CH₂) |
| (79) | 5-(pyrazin-2-yl)pyridin-2-yl methylene |
| (80) | 6-(5-CH₂-thiophen-2-yl)pyridine-2-carbonitrile |
| (81) | 2,2'-bipyridin-5-yl methylene |
| (82) | 6'-amino-2,2'-bipyridin-5-yl methylene |
| (83) | 6-(5-CH₂-isoxazol-3-yl)pyridine-2-carboxamide |
| (84) | 6-aminopyridin-3-yl propylene |
| (85) | 6-cyanopyridin-3-yl methylene |
| (86) | 5-(5-cyanothiophen-2-yl)isoxazol-3-yl methylene |
| (87) | 6-(1H-1,2,4-triazol-1-yl)pyridin-3-yl methylene |
| (88) | 6-(1H-imidazol-1-yl)pyridin-3-yl methylene |
| (89) | 6-ethynylpyridin-3-yl methylene |

TABLE 1-continued

| Compound | R$_{12}$ |
|---|---|
| (90) | (2-aminopyridin-6-yl)methyl |
| (91) | 1-(pyrimidin-2-yl)-1H-imidazol-4-yl methyl |
| (92) | (5-amino-1,3,4-thiadiazol-2-yl)methyl |
| (93) | 6-(5-amino-1,3,4-thiadiazol-2-yl)pyridin-3-yl methyl |
| (94) | 5-(5-amino-1,3,4-thiadiazol-2-yl)pyridin-2-yl methyl |
| (95) | (6-aminopyridin-2-yl)ethynyl-propyl |
| (96) | (6-aminopyridin-2-yl)vinyl-propyl |
| (97) | (1H-pyrrolo[2,3-b]pyridin-6-yl)vinyl-CH$_2$OCH$_2$- |
| (98) | 6-(1,3,4-thiadiazol-2-yl)pyridin-3-yl methyl |
| (99) | 6-(1H-pyrazol-1-yl)pyridin-3-yl propyl |
| (100) | 5-(1H-pyrazol-1-yl)pyrimidin-2-yl propyl |
| (101) | 6-(3-(thiophen-2-yl)-1H-pyrazol-1-yl)pyridin-3-yl propyl |
| (102) | 2-amino-3-(pyrimidin-2-yl)pyridin-6-yl vinyl-propyl |
| (103) | 1H-indazol-6-yl vinyl-propyl |
| (104) | (2-aminobenzo[d]thiazol-6-yl)vinyl-CH$_2$OCH$_2$CH$_3$ |
| (105) | (2-amino-1H-benzo[d]imidazol-5-yl)ethyl-OCH$_2$CH$_2$- |

TABLE 1-continued

| Compound | R$_{12}$ |
|---|---|
| (106) | 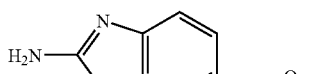 |
| (107) | 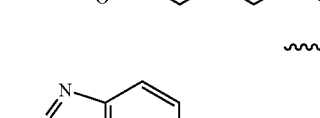 |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art, or a pharmaceutically acceptable salt, ester, or prodrug thereof, with a pharmaceutically acceptable carrier or excipient.

In addition, the present invention contemplates processes of making any compound delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system having one or two aromatic rings including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The terms "$C_1$-$C_6$ alkyl," or "$C_1$-$C_{12}$ alkyl," as used herein, refer to saturated, straight- or branched-chain hydrocarbon radicals containing between one and six, or one and twelve carbon atoms, respectively. Examples of $C_1$-$C_6$ alkyl radicals include, but are not limited to, methyl, ethyl, propyl, isopropyl, n-butyl, tert-butyl, neopentyl and n-hexyl radicals; and examples of $C_1$-$C_{12}$ alkyl radicals include, but are not limited to, ethyl, propyl, isopropyl, n-hexyl, octyl, decyl, dodecyl radicals.

The term "$C_2$-$C_6$ alkenyl," as used herein, denotes a monovalent group derived from a hydrocarbon moiety containing from two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "$C_2$-$C_6$ alkynyl," as used herein, denotes a monovalent group derived from a hydrocarbon moiety containing from two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "$C_1$-$C_8$ alkylene," as used herein, refer to saturated, straight- or branched-chain hydrocarbon containing between one and eight. Alkylene groups include, but are not limited to, ethylene, propylene, butylene, 3-methyl-pentylene, and 5-ethyl-hexylene.

The term "$C_2$-$C_8$ alkenylene," as used herein, denotes a divalent group derived from a straight chain or branch hydrocarbon moiety containing from two to eight carbon atoms having at least one carbon-carbon double bond. Alkenylene groups include, but are not limited to, for example, ethenylene, 2-propenylene, 2-butenylene, 1-methyl-2-buten-1-ylene, and the like.

The term "$C_2$-$C_8$ alkynylene," as used herein, denotes a divalent group derived from a straight chain or branch hydrocarbon moiety containing from two to eight carbon atoms having at least one carbon-carbon triple bond. Representative alkynylene groups include, but are not limited to, for example, propynylene, 1-butynylene, 2-methyl-3-hexynylene, and the like.

The terms "substituted aryl", "substituted heteroaryl," "substituted $C_1$-$C_6$ alkyl," or "substituted $C_1$-$C_{12}$ alkyl," "substituted $C_2$-$C_6$ alkenyl," "substituted $C_2$-$C_6$ alkynyl," "substituted $C_1$-$C_8$ alkylene," "substituted $C_2$-$C_8$ alkenylene," "substituted $C_2$-$C_8$ alkynylene," as used herein, refer to aryl, heteroaryl, $C_1$-$C_6$ alkyl, $C_1$-$C_{12}$ alkyl, $C_2$-$C_6$ alkenyl, $C_2$-$C_6$ alkynyl, $C_1$-$C_8$ alkylene, $C_2$-$C_8$ alkenylene, substituted $C_2$-$C_8$ alkynylene groups as previously defined, substituted by independent replacement of one, two, or three or more of the hydrogen atoms thereon with substituents including, but not limited to, —F, —Cl, —Br, —I, —OH, protected hydroxyl, —NO$_2$, —CN, —C$_1$-C$_{12}$-alkyl optionally substituted with, for example, halogen, C$_2$-C$_{12}$-alkenyl optionally substituted with, for example, halogen, —C$_2$-C$_{12}$-alkynyl optionally substituted with, for example, halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl,-dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—

$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_2$-alkenyl, —$OCO_2$—$C_2$-$C_2$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH— aryl, —OCONH— heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$— aryl, —$NHCO_2$— heteroaryl, —$NHCO_2$— heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_2$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_2$-cycloalkyl, —NHC(NH)NH-aryl, —NHC(NH)NH-heteroaryl, —NHC(NH)NH-heterocycloalkyl, —NHC(NH)—$C_1$-$C_2$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_2$-alkenyl, —C(NH)NH—$C_2$-$C_2$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH—aryl, —$SO_2$NH— heteroaryl, —$SO_2$NH— heterocycloalkyl, —$NHSO_2$—$C_1$-$C_{12}$-alkyl, —$NHSO_2$—$C_2$-$C_{12}$-alkenyl, —$NHSO_2$—$C_2$-$C_2$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_2$-alkyl, —S—$C_2$-$C_{12}$-alkenyl, —S—$C_2$-$C_{12}$-alkenyl, —S—$C_3$-$C_2$-cycloalkyl, —S-aryl, —S-heteroaryl, —S-heterocycloalkyl, or methylthiomethyl. It is understood that the aryls, heteroaryls, alkyls, and the like can be further substituted.

In accordance with the invention, any of the aryls, substituted aryls, heteroaryls and substituted heteroaryls described herein, can be any aromatic group. Aromatic groups can be substituted or unsubstituted.

The term "$C_3$-$C_{12}$-cycloalkyl," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

It is understood that any alkyl, alkenyl, alkynyl and cycloalkyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reactions. Examples of hydroxyl activating group include, but not limited to, mesylate, tosylate, triflate, p-nitrobenzoate, phosphonate and the like.

The term "activated hydroxyl", as used herein, refers to a hydroxy group activated with a hydroxyl activating group, as defined above, including mesylate, tosylate, triflate, p-nitrobenzoate, phosphonate groups, for example.

The term "hydroxyl protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts,

*Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxyl," as used herein, refers to a hydroxy group protected with a hydroxy protecting group, as defined above, including benzoyl, acetyl, trimethylsilyl, triethylsilyl, methoxymethyl groups, for example.

The term "hydroxyl prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs. Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —NH(C$_1$-C$_{12}$ alkyl) where C$_1$-C$_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxyl acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19(1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, meningitis, sinusitus, bronchitis, tonsillitis, cystic fibrosis (CF) and mastoiditis related to infection by *Streptococcus pneumoniae, Haemophilus influenzae, Moraxella catarrhalis, Staphylococcus aureus, Peptostreptococcus* spp, or *Pseudomonas* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C—F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S. and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica, P. multocida, Mycoplasma* bovis, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae., P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 ug/ml to about 0.03 ug/ml. The diluted compounds (2 ul/well) are then transferred into sterile, uninoculated CAMHB (0.2 mL) by use of a 96 fixed tip-pipetting station. The inoculum for each bacterial strain is standardized to $5 \times 10^5$ CFU/mL by optical comparison to a 0.5 McFarland turbidity standard. The plates are inoculated with 10 ul/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 ug/ml to about 0.03 ug/ml.

All in vitro testing follows the guidelines described in the Approved Standards M7-A4 protocol, published by the National Committee for Clinical Laboratory Standards (NC-CLS).

The invention further provides compositions and methods of treating patients suffering from an inflammatory condition comprising administering to a patient in need thereof, a therapeutically effective amount of at least one compound of the invention, A or B. Specific examples of inflammatory conditions treatable according to the invention include, but are not limited to, scleritis; epi-scleritis; allergic conjunctivitis; pulmonary inflammatory diseases, particularly CF, asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those patients susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention any compound of the invention is administered to a patient in need of treatment for CF, in amount sufficient to prevent, diminish or eradicate symptoms of CF including chronic pulmonary inflammation and infection.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

According to the methods of treatment of the present invention, bacterial infections, cystic fibrosis and inflammatory conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such intramuscularly, or subcutaneously; or orally, buccally, nasally, transmucosally, administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AcOH for acetic acid;
AIBN for azobisisobutyronitrile;
$Boc_2O$ for di-tert-butyl-dicarbonate;
Boc for t-butoxycarbonyl;
Bpoc for 1-methyl-1-(4-biphenylyl)ethyl carbonyl;
Bz for benzoyl;
Bn for benzyl;
BocNHOH for tert-butyl N-hydroxycarbamate;
t-BuOK for potassium tert-butoxide;
$Bu_3SnH$ for tributyltin hydride;
BOP for (benzotriazol-1-yloxy)tris(dimethylamino)phosphonium Hexafluorophosphate;
Brine for sodium chloride solution in water;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
CuCl for copper (I) chloride;
CuI for copper (I) iodide;
dba for dibenzylidene acetone;
dppb for diphenylphosphino butane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or $(i-Pr)_2EtN$ for N,N,-diisopropylethyl amine;

Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
Et$_2$O for diethyl ether;
HATU for O-(7-azabenzotriazol-1-yl)-N,N,N',N',-tetramethyluronium Hexafluorophosphate;
HCl for hydrogen chloride;
HOBT for 1-hydroxybenzotriazole;
K$_2$CO$_3$ for potassium carbonate;
MeOH for methanol;
Mg for magnesium;
MOM for methoxymethyl;
Ms for mesyl or —SO$_2$—CH$_3$;
Ms$_2$O for methanesulfonic anhydride or mesyl-anhydride;
NaN(TMS)$_2$ for sodium bis(trimethylsilyl)amide;
NaCl for sodium chloride;
NaH for sodium hydride;
NaHCO$_3$ for sodium bicarbonate or sodium hydrogen carbonate;
Na$_2$CO$_3$ sodium carbonate;
NaOH for sodium hydroxide;
Na$_2$SO$_4$ for sodium sulfate;
NaHSO$_3$ for sodium bisulfite or sodium hydrogen sulfite;
Na$_2$S$_2$O$_3$ for sodium thiosulfate;
NH$_2$NH$_2$ for hydrazine;
NH$_4$HCO$_3$ for ammonium bicarbonate;
NH$_4$Cl for ammonium chloride;
NMMO for N-methylmorpholine N-oxide;
NaIO$_4$ for sodium periodate;
Ni for nickel;
OH for hydroxy
OsO$_4$ for osmium tetroxide
TEA or Et$_3$N for triethylamine;
TFA trifluoroacetic acid
THF for tetrahydrofuran;
TPP or PPh$_3$ for triphenylphosphine;
Troc for 2,2,2-trichloroethyl carbonyl
Ts for tosyl or —SO$_2$—C$_6$H$_4$CH$_3$;
Ts$_2$O for tolylsulfonic anhydride or tosyl-anhydride;
TsOH for p-tolylsulfonic acid;
Pd for palladium;
Ph for phenyl;
POPd for dihydrogen dichlorobis(di-tert-butylphosphinito-☐P)palladate(II);
Pd$_2$(dba)$_3$ for tris(dibenzylideneacetone) dipalladium (0);
Pd(PPh$_3$)$_4$ for tetrakis(triphenylphosphine)palladium (0);
PdCl$_2$(Ph$_3$P)$_2$ for trans-dichlorobis(triphenylphosphine) palladium (II);
Pt for platinum;
Rh for rhodium;
Ru for ruthenium;
TBS for tert-butyl dimethylsilyl; or
TMS for trimethylsilyl;
TMSCl for trimethylsilyl chloride Synthetic Methods The compounds and processes of the present invention will be better understood in connection with the following synthetic schemes that illustrate the methods by which the compounds of the invention may be prepared.

A preferred intermediate for the preparation of compounds represented by formula I is a compound represented by formula (1.1) as illustrated below,

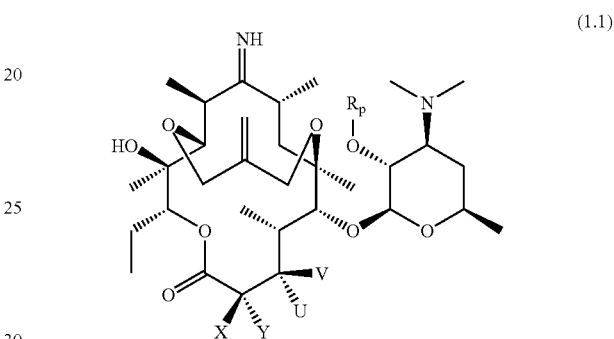

wherein R$_p$, U, V, X, and Y are as previously defined.

A second preferred intermediate for the preparation of compounds represented by formula I is a compound represented by formula (1.2) as illustrated below,

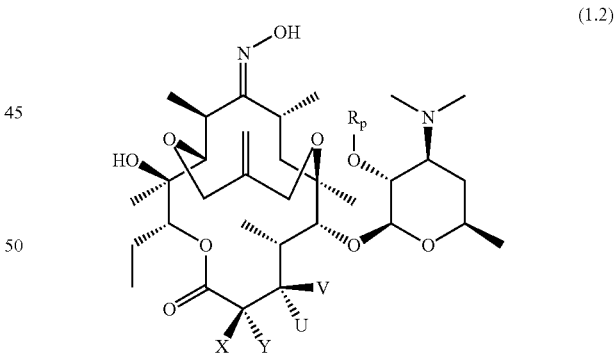

wherein R$_p$, U, V, X, and Y are as previously defined.

Scheme 1-6 describe processes for the preparation of compounds according to the invention.

Compounds of formula (1.1) and (1.2), which are useful as the starting materials for the preparation of compounds of the present invention are prepared from erythromycin using the procedures described in U.S. Patents US 2004/0053861 and US 2004/0157787.

Scheme 1

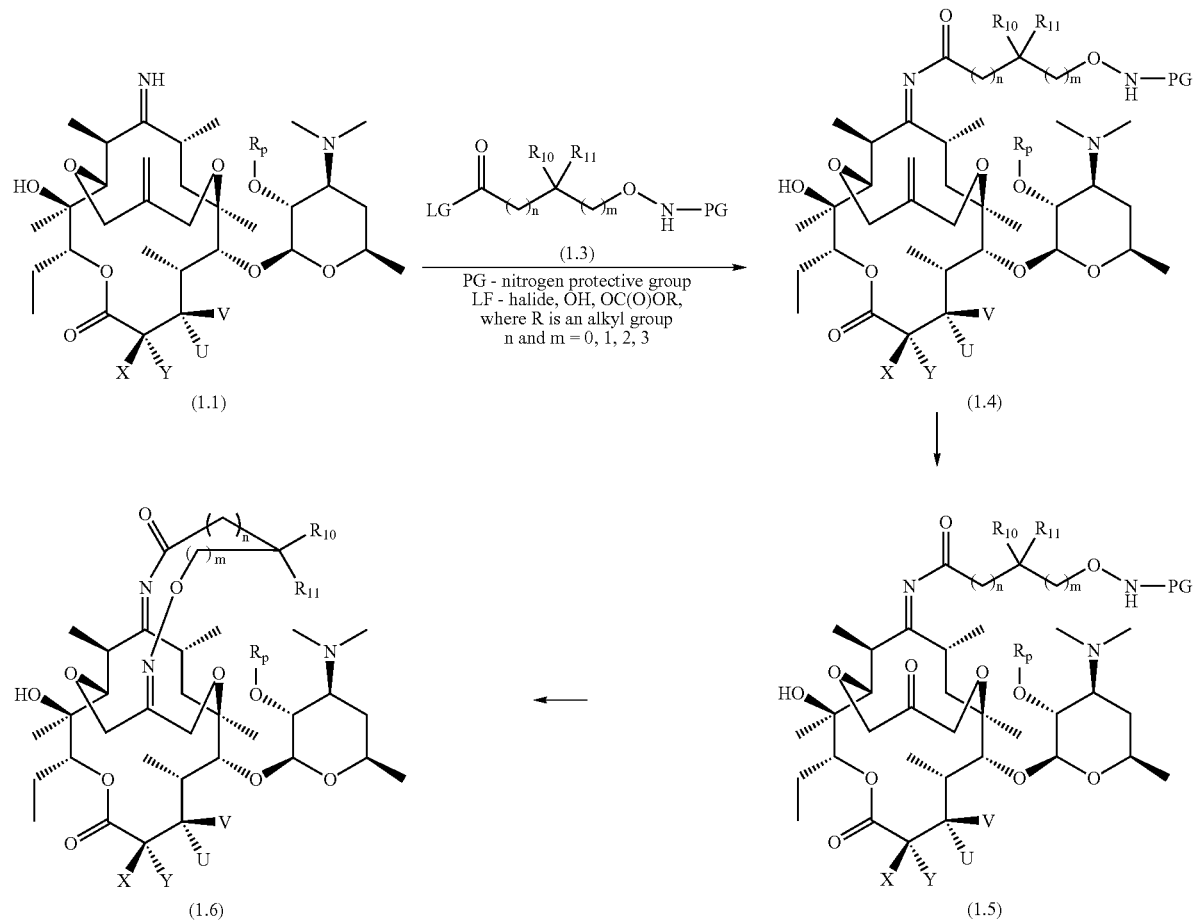

As shown in Scheme 1, conversion of imine (1.1) to a compound of formula (1.4) can be accomplished by coupling with an activated carboxylic acid (1.3) such as acyl halides or mixed anhydrides of a carboxylic acid of formula $PGNH_2O(CH_2)_mC(R_5)(R_6)(CH_2)_nCO_2H$ in the presence of an appropriate base including, but not limited to, triethylamine, pyridine, diisopropylethylamine, and the like, optionally in the presence of a catalyst such as DMAP. The reaction is typically carried out in aprotic solvents including, but not limited to, dichloromethane, DMF, DMSO, THF, and the like, or combination thereof, at 0° C. to 80° C. for 5 to 24 hours. Alternatively, conversion of imine (1.1) to the compound (1.4) can be accomplished by coupling with a carboxylic acid (1.3) in the presence of appropriate coupling reagent and base in a polar aprotic solvent at −20° C. to 80° C. for 1 to 48 hours. The amino group of α-hydroxylamine carboxylic acids (1.3) having formula $NH_2O(CH_2)_mC(R_5)(R_6)(CH_2)_nCO_2H$ has to be protected with an amino protecting group such as, but not limited to, 2,2,2-trichloroethyl carbonyl (Troc), 1-methyl-1-(4-biphenylyl)ethyl carbonyl (Bpoc), succinimide, phthalimide, t-butyloxycarbonyl (Boc), and the like. The preferred protecting group for carboxylic acids (1.3) is t-butyloxycarbonyl (Boc). A more thorough discussion of solvents and conditions for protecting the amino group can be found in T. W. Greene and P. G. M. Wuts, *"Protective Groups in Organic Synthesis"*, $3^{rd}$ ed., 1999.

Examples of appropriate coupling reagents include, but are not limited to, N-(3-dimethylaminopropyl)-N'-ethylcarbodiimide, (benzotriazol-1-yloxy)tris(dimethylamino) phosphonium hexafluorophosphate, O-(7-azabenzotriazol-1-yl)-N,N,N',N'-tetramethyluronium hexafluorophosphate, N,N'-dicyclohexylcarbodiimide, 1-hydroxybenzotriazole, and the like. Examples of bases include, but are not limited to, triethylamine, pyridine, DMAP, diisopropylethylamine, N-methylmorpholine, N-ethylmorpholine, and the like. Examples of solvents for this reaction include polar aprotic solvents such as, but not limited to, dichloromethane, 1,2-dichloroethane, dioxane, THF, DMF, acetonitrile, and the like, or mixture thereof. The preferred temperature of the reaction is around 25° C.

The bridged olefin of the compound (1.4) can be converted to a ketone compound of formula (1.5) by an oxidative cleavage. Oxidative cleavage may be performed, for example, by ozonolysis or by treatment with an oxidant followed by addition of a cleaving reagent. Ozonolysis may be achieved by treating the olefin of a compound of formula (1.4) with ozone followed by decomposition of the ozonide with an appropriate reducing agent. Suitable reducing agents for this process include, but are not limited to, dimethyl sulfide, zinc, trivalent phosphorous compounds, sodium sulfite, and the like. The reaction is typically carried out in an inert solvent such as, but not limited to, methanol, ethanol, ethyl acetate, glacial acetic acid, chloroform, methylene chloride., hexanes or mixtures thereof, preferably at −78° to −20° C. Preferred reducing agents include, but are not limited to, triphenylphosphine, trimethyl phosphite, thiourea, and dimethyl sulfide, and the like. A more thorough discussion of ozonolysis and the conditions there for can be found in J. March "Advanced Organic Chemistry" 4$^{th}$ ed., Wiley & Son, Inc, 1992.

An alternative method for the preparation of a compound of formula (1.5) involves dihydroxylation of the alkene compound of formula (1.4) by an oxidant followed by cleavage of diol with a cleaving reagent. The glycol is first prepared by reacting the alkene (1.4) with an oxidant. Suitable oxidants for the present process include, but are not limited to, osmium tetroxide, optionally, in the presence of an additional oxidant such as hydrogen peroxide, t-butyl hydroperoxide, N-methylmorpholine-N-oxide, or barium chlorate. Dihydroxylation reactions can be carried out in a variety of solvents including 1,4-dioxane, tetrahydrofuran, tert-butanol, and diethyl ether, preferably at a temperature between 0° C. and 50° C.

The resulting glycol can be cleaved by a variety of cleaving reagents including, but not limited to, periodic acid, lead tetraacetate, manganese dioxide, potassium permanganate, sodium metaperiodate, sodium periodate, and N-iodosuccinimide. A preferred cleaving reagent is sodium periodate. The preferred solvents include a mixture of one of these solvents such as ethanol, methanol, acetone, acetonitrile, 1,4-dioxane, isopropanole, acetone, water, and the like or combination thereof. The temperature of the reaction varies from about −10° C. to approximately 50° C. Optionally the oxidation of the bridged olefin to the diol, followed by its cleavage to the ketone can be accomplished in one operation in the presence of, for example, a catalytic amount of osmium tetraoxide with an excess amount of sodium periodate to provide compound (1.5).

The conversion of the compound (1.5) to compound (1.6) can be accomplished directly during deprotection of the amino group of compound (1.5), wherein the unprotected hydroxylamine intermediate couples with the bridged ketone under deprotection conditions to give compound (1.6). Since the preferred protective group of hydroxylamine is t-butyloxycarbonyl (Boc), it is removed under acidic conditions. Examples of acids used to deprotect a Boc-protecting group include, but are not limited to, hydrochloric acid, trifluoroacetic acid, p-tolylsulfonic acid, and the like, in solvents such as, but not limited to, ethyl acetate, methanol, THF, dichloromethane, dioxane, chloroform, water, and the like, or combination thereof at −10° C. to 110° C. for 0.5 to 12 hours. The preferred reaction condition for conversion of compound (1.5) to compound (1.6) is treating compound (1.5) with trifluoroacetic acid in dichloromethane at around 0° C. for 0.5 to 2 hours.

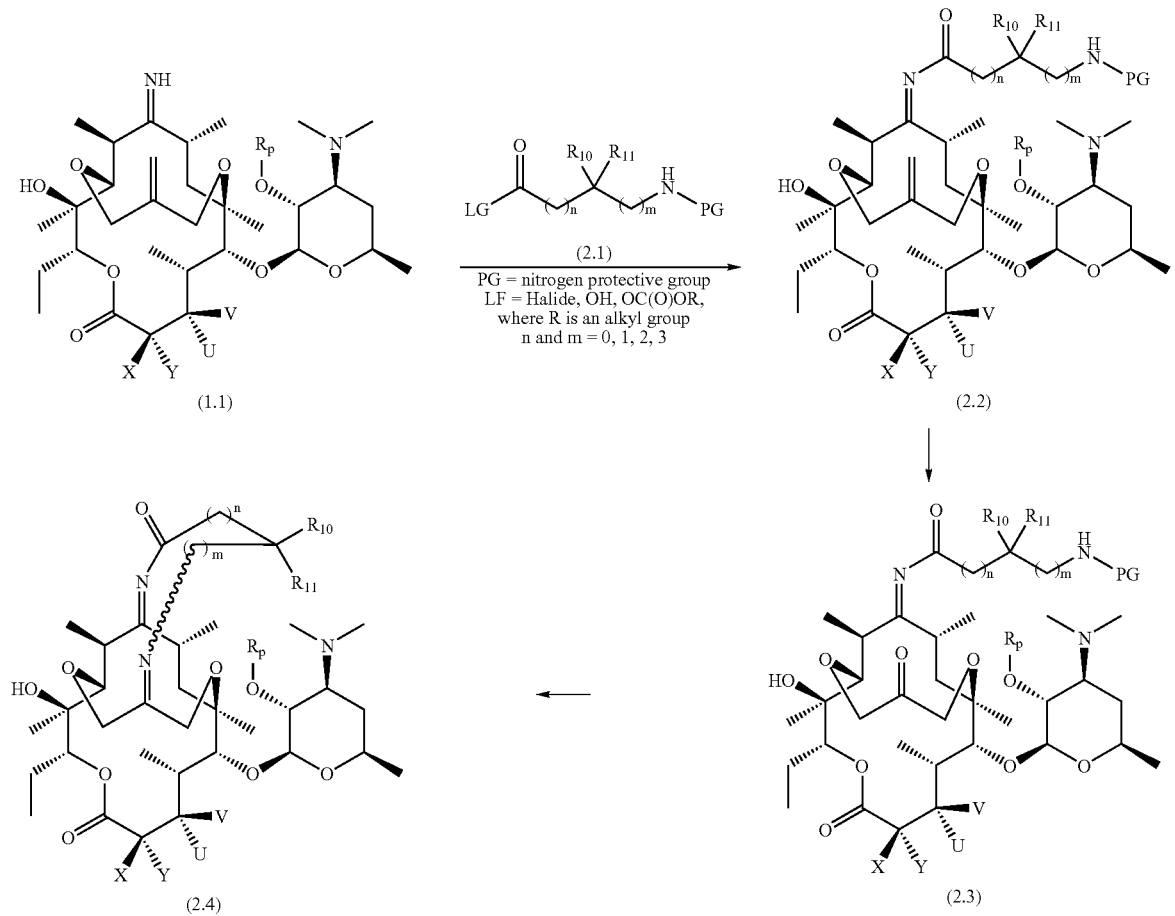

As shown in Scheme 2, the conversion of imine (1.1) to a compound of formula (2.2) can be accomplished by coupling of compound of formula (1.1) with an activated carboxylic acid (2.1) such as acyl halides or mixed anhydrides of a carboxylic acid of formula $NH_2(CH_2)_m C(R_5)(R_6)(CH_2)_n CO_2H$ in the presence of an appropriate base such as, but not limited to, triethylamine, pyridine, diisopropylethylamine and the like, optionally in the presence of catalyst such as DMAP. The reaction is typically carried out in aprotic solvents such as, but not limited to, dichloromethane, DMF, DMSO, THF, and the like, or combination thereof, at 0° C. to 80° C. for 5 to 24 hours. An alternative method for the preparation of a compound of formula (2.2) involves coupling of an imine of a formula (1.1) with a carboxylic acid (2.1) in the presence of appropriate coupling reagent and base in a polar aprotic solvent at −20° to 80° C. for 1 to 48 hours. Examples of appropriate coupling reagents include, but are not limited to, EDC, BOP, HATU, DCC, HOBT and the like. Examples of bases include, but are not limited to, $Et_3N$, pyridine, DMAP, diisopropylethylamine, N-methylmorpholine, N-ethylmorpholine, and the like. Examples of solvents for this reaction include polar aprotic solvents such as, but not limited to, dichloromethane, 1,2-dichloroethane, dioxane, THF, DMF, acetonitrile, and the like, and mixture thereof. The preferred temperature of the reaction is around 25° C.

The olefin of compound (2.2) can be converted to a ketone compound of formula (2.3) by an oxidative cleavage. Oxidative cleavage may be performed by, for example, ozonolysis or by treatment with an oxidant followed by the cleaving reagent. The details of this step are described in Scheme 1 of this invention.

The conversion of compound (2.3) to compound (2.4) can be accomplished directly during deprotection of the amino group of compound (2.3), wherein the unprotected amine intermediate couples directly with the bridged ketone under deprotection conditions to give compound (2.4).

Scheme 3

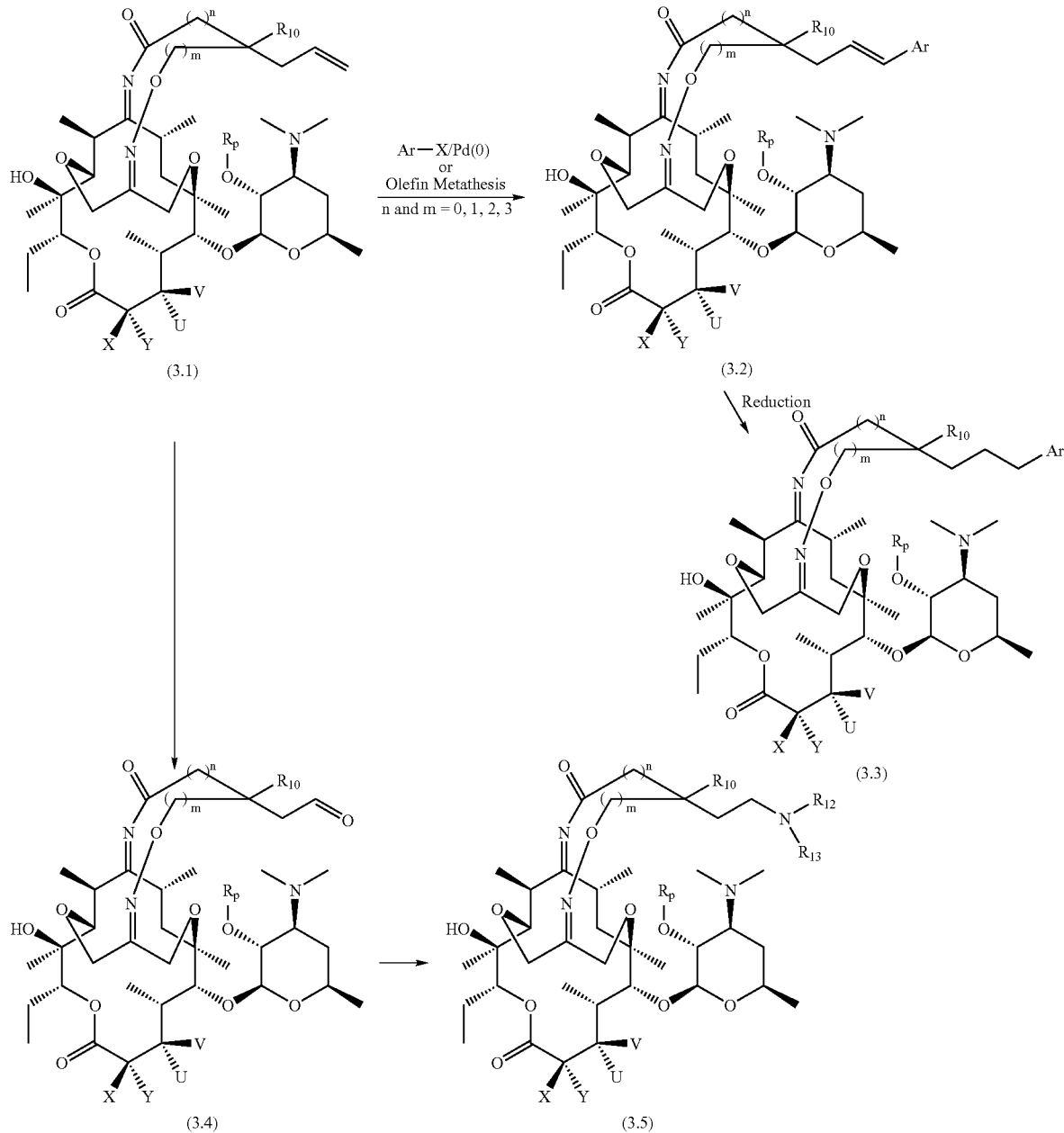

A compound of formula (3.1) is equivalent to the compound of general formula (1.5), where $R_{11}$ is —$CH_2CH=H_2$ and can be prepared by the synthetic route described in Scheme 1 of this invention. A compound of formula (3.2) can be prepared by several different ways. First, in a Heck coupling reaction, a compound of formula (3.1) can be treated with an aryl halide or aryl triflate in the presence of a palladium catalyst [Pd(0) or Pd(II)]to provide compound (3.2) (Ref.: Heck, Palladium Reagents in Organic Synthesis, Academic Press: New York, 1985, Chapter 1). Under the conditions of Heck coupling reaction, mixtures of regio and stereo isomers of the double bond are possible. Alternatively, a compound of formula (3.1) can undergo a cross metathesis reaction with vinylaromatic or vinylheteroaromatic derivatives using ruthenium catalysts in solvents such as, but not limited to, dichloromethane, 1,2-dichloroethatne, and the like, at 20° C. to 80° C. for one to 72 hours. (Ref: (a) *J. Org. Chem.* 2000, 65, 2204-2207; (b) Reviews: *Synlett.* 1999, 2, 267; (c) Reviews; Irvin, K. J.; Mol, J. C. Olefin Metathesis and Metathesis Polymerization, $2^{nd}$ ed.; Academic Press: New York, 1997; (d) *J. Org. Chem.* 1999, 64, 4798-4816; (e) *Angew. Chem., Int. Ed. Engl.* 1997, 36, 2036-2056; (f) *Tetrahedron* 1998, 54, 4413-4450).

A double bond of compound (3.2) can be further reduced with reagents such as, but not limited to, hydrogen, ammonium formate, tri-n-butyltin hydride, triethylsilane, and the like, in the presence of a metal catalyst such as Pd, Rh, Pt, Ru, Mg, Ni, and the like, in solvents such as methanol, ethanol, ethylacetate, isopropanol, $Et_2O$, water, DMF, and the like, or mixture thereof to give a compound (3.3).

A double bond of compound (3.1) can be converted to an aldehyde of formula (3.4) by an oxidative cleavage. Oxidative cleavage may be performed by treating compound (3.1) with a mixture of a catalytic amount of $OsO_4$ and an excess of $NaIO_4$ in solvents such as, but are not limited to, acetonitrile, acetone, water, dioxane, and the like, or combination thereof, at −10° C. to 50° C. for 0.5 to 5 hours to give compound of formula (3.4). Alternatively, oxidative cleavage can be performed by ozonolysis. Ozonolysis may be achieved by treating the olefin of compound (3.1) with ozone followed by decomposition of the ozonide by an appropriate reducing agent. Suitable reducing agents for this process include, but are not limited to, dimethyl sulfide, zinc, trimethoxyphosphite, triphenylphosphine, and the like. The reaction is typically carried out in solvent such as, but not limited to, methanol, ethanol, ethyl acetate, glacial acetic acid, chloroform, methylene chloride, or mixtures thereof, preferably at −78° to 0° C.

Further, an aldehyde of formula (3.4) can be converted to amine derivatives of formula (3.5) by reductive amination. Reductive amination can be performed by treating compound (3.4) with an amine in the presence of sodium cyanoborohydride, and the like, at a pH from 2 to about 5, in solvents such as, but not limited to, methanol, ethanol, isopropanol, water, acetonitrile, and the like, or combination thereof, at −10° C. to 25° C. to give corresponding amine of formula (3.5).

Scheme 4

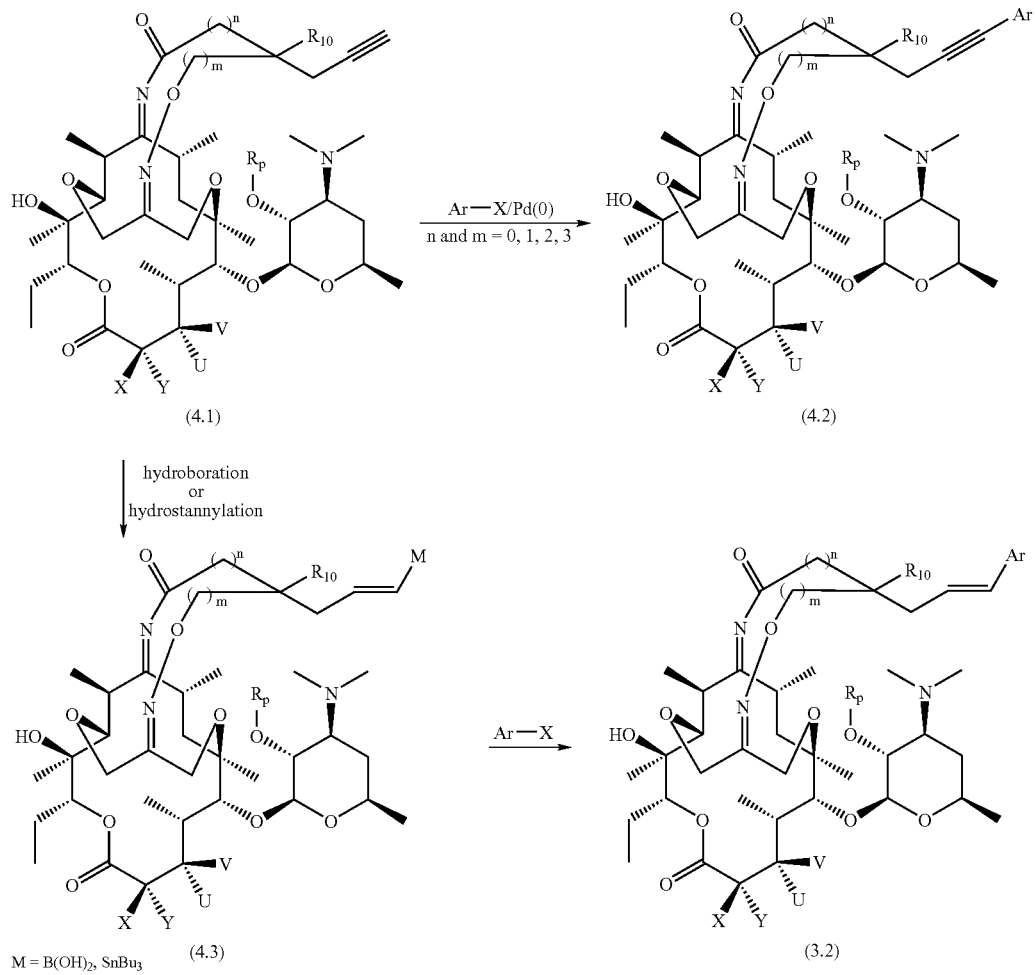

A compound of formula (4.1) can be prepared by the synthetic route described in Scheme 1 of this invention. As shown in Scheme 4, conversion of compound (4.1) to compound (4.2) can be accomplished by coupling with different unsubstituted or substituted aryl halides, or unsubstituted or substituted heteroaryl halides in the presence of a palladium catalyst [Pd(0) or Pd(II)], optionally in the presence of a base and optionally in the presence of a ligand, and in the presence of a catalytic amount of CuI in an aprotic solvent at 25° C. to 100° C. for 2 to 20 hours. Examples of palladium (0) or palladium (II) catalysts include, but are not limited to, $Pd(PPh_3)_4$, $Pd_2(dba)_3$, $PdCl_2(Ph_3P)_2$, and the like. Examples of a ligand include but not limited to $PPh_3$, diphenylphosphinoethane, triphenylarsine, and the like. Examples of base include, but are not limited to, triethylamine, pyridine, and the like. The reaction is typically carried out in aprotic solvents such as, but are not limited to, THF, acetonitrile, DME, DMF, DMSO, and the like, or mixtures thereof, (Ref.: (a) Sonogashira, Comprehensive Organic Synthesis, Volume 3, Chapters 2 and 4; (b) Sonogashira, Synthesis 1977, 777). Alternatively, the propargyl group of compound (4.1) can be reduced with a variety of borane or stannane reagents to give vinyl boronic acid or vinylstannyne of formula (4.3), that can be further used in Suzuki or Stille coupling reaction with different aryl or heteroaryl halides or triflates in the presence of a palladium catalyst [Pd(0), or Pd(II)] to provide compound (3.2) (Ref.: (Suzuki, Chemical Reviews, 1995, 95, 2457; (b) Suzuki, Pure & Appl. Chem. 1991, 63, 419).

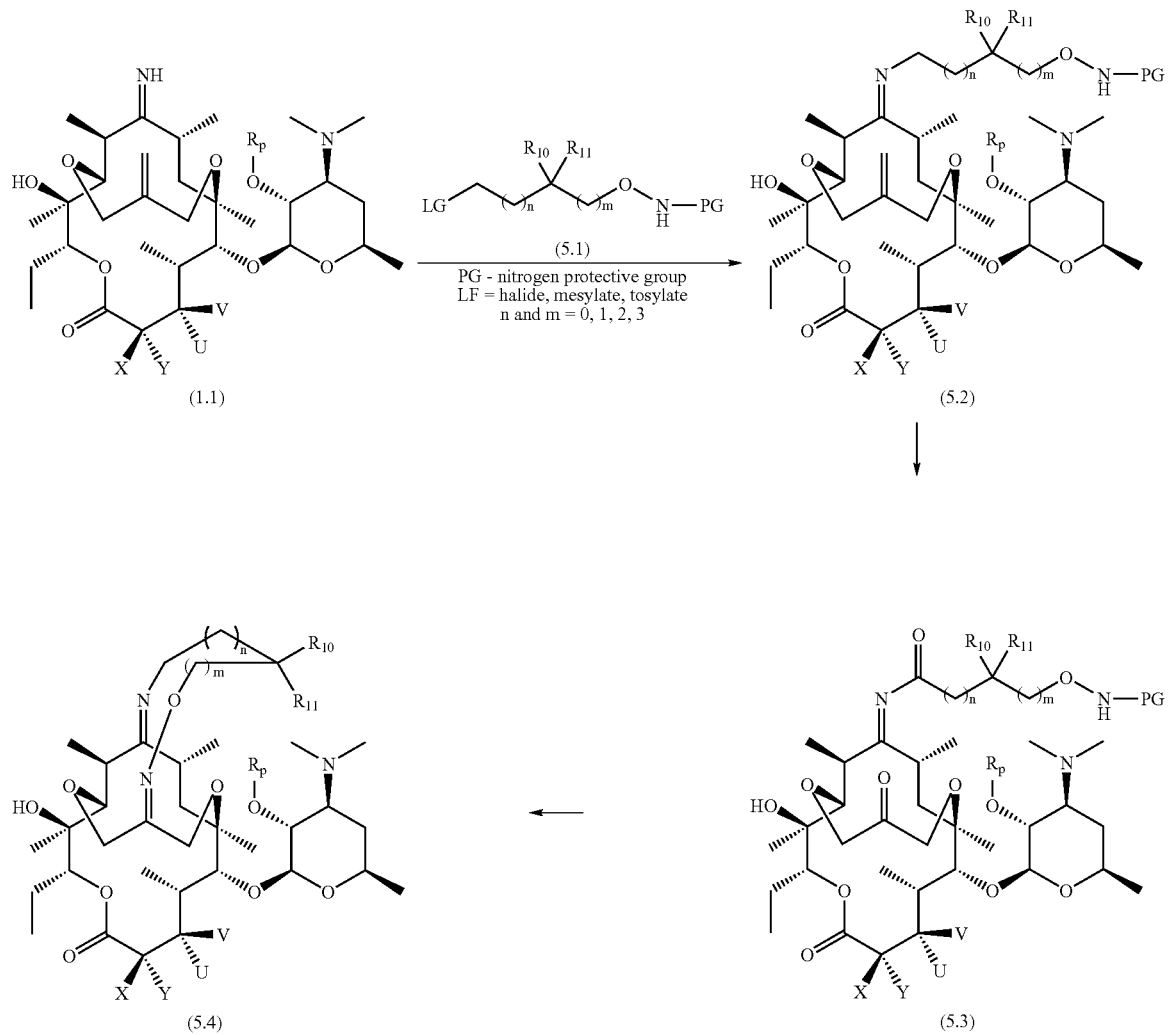

Scheme 5

As shown in Scheme 5, conversion of imine (1.1) to a compound of formula (5.2) can be accomplished by coupling with alkylating reagents of formula (5.1) in the presence of base in polar aprotic solvents at 0° C. to 140° C. for 3 to 24 hours. Examples of base include, but are not limited to, $K_2CO_3$, $Na_2CO_3$, NaH, t-BuOK, and the like. The reaction is typically carried out in aprotic solvents such as, but not limited to, THF, DMF, DME, acetonitrile, and the like, or mixtures thereof.

Bridged olefin of compound (5.2) can be converted to a ketone of formula (5.3) by an oxidative cleavage. Details of possible ways of oxidative cleavage are described in Scheme 1 of the present invention.

The conversion of the compound (5.3) to compound (5.4) can be accomplished directly during deprotection of the amino group of compound (5.3), wherein the unprotected hydroxylamine intermediate reacts with bridged ketone under deprotection conditions to give compound (5.4). Details of this transformation are described in Scheme 1 of this invention.

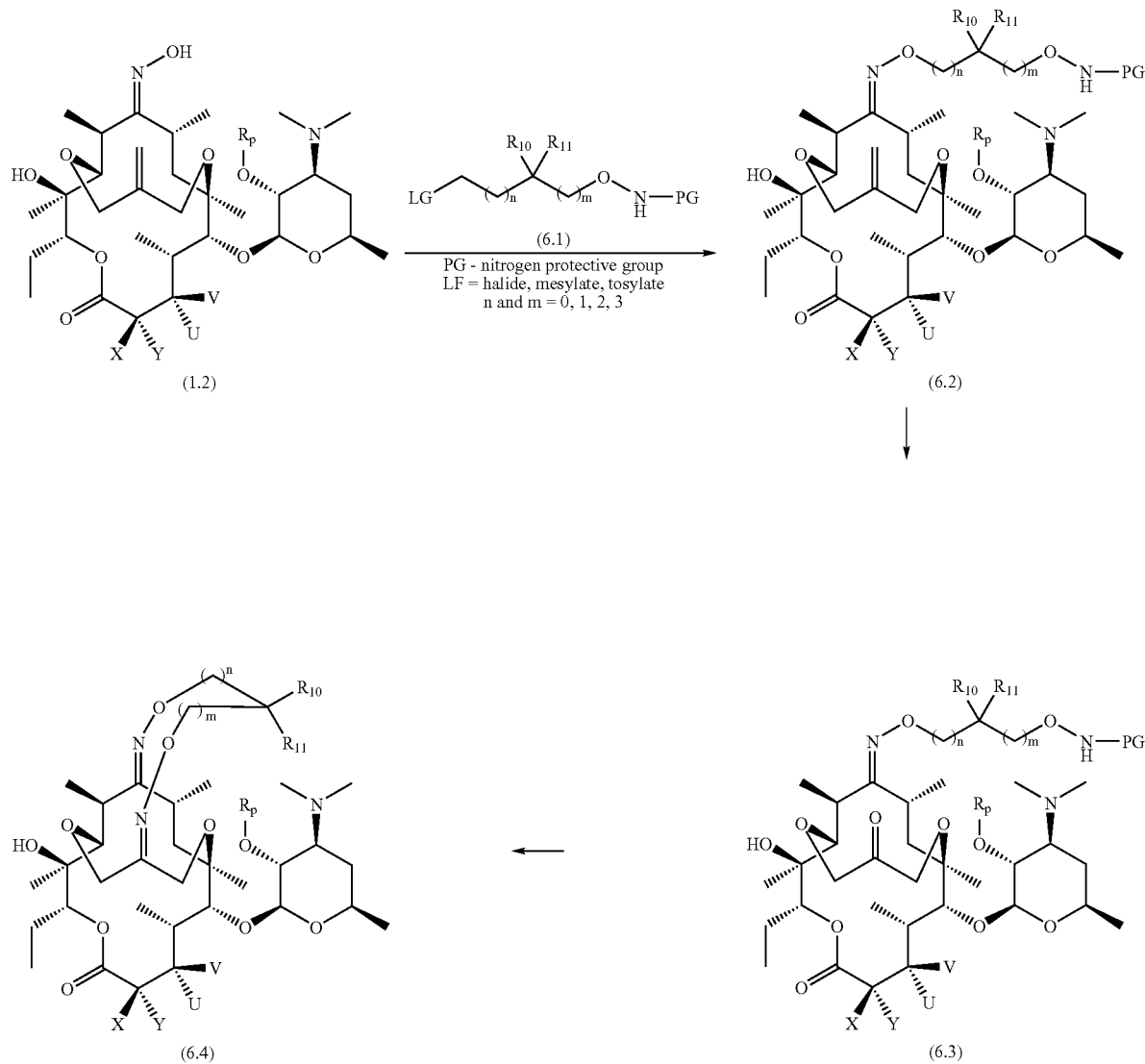

As shown in Scheme 6, conversion of oxime (1.2) to a compound of formula (6.2) can be accomplished by coupling with alkylating reagents of formula (6.1) in the presence of a base in polar aprotic solvents at 0° C. to 140° C. for 3 to 24 hours.

Examples of base include, but are not limited to, $K_2CO_3$, $Na_2CO_3$, NaH, t-BuOK, and the like. The reaction is typically carried out in aprotic solvents such as, but not limited to, THF, DMF, DME, acetonitrile, and the like, or mixtures thereof.

Bridged olefin of the compound (6.2) can be converted to a ketone compound of formula (6.3) by an oxidative cleavage. Details of possible ways of oxidative cleavage are described in Scheme 1 of the present invention.

The conversion of compound (6.3) to compound (6.4) can be accomplished directly during deprotection of the amino group of compound (6.3), wherein the unprotected hydroxylamine intermediate reacts with bridged ketone under deprotection conditions to give compound (6.4). Details of this transformation are described in Scheme 1 of this invention.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula (IV): $R_{10}=R_{11}=H$, $R_p=Ac$, $U=OH$, $V=H$, $X=CH_3$, $Y=H$ Step 1a. Compound (1.4) of Scheme (1): $n=m=0$, $R_{10}=R_{11}=H$, $R_p=Ac$, $PG=Boc$, $U=OH$, $V=H$, $X=CH_3$, $Y=H$ To a solution of compound (1.1) of Scheme 1 (where $R_p=Ac$, $U=OH$, $X=CH_3$ and V and Y are hydrogen) (7.0 g, 10.48 mmol) and (Boc-aminooxy) acetic acid (4.05 g, 21.18 mmol) in $CH_2Cl_2$ (50 mL) was added EDC.HCl (4.07 g, 26.26 mmol) and diisopropylethyl amine (9.2 mL, 52.82 mmol) at room temperature. The reaction mixture was stirred for 24 hours at room temperature. The reaction mixture was quenched by saturated sodium bicarbonate. The resulting mixture was extracted with $CH_2Cl_2$ (50 mL×3). The combine organic layers were washed with saturated $NaHCO_3$ (50 mL×2) and brine, dried ($Na_2SO_4$) and filtered. The filtrate was concentrated to give 8.80 g of the crude product, which was purified by flash chromatography (silica gel, acetone/hexane=1/3 to 1/2) to afford 5.10 g (58%) of the title compound. MS (ESI) m/z=842 $(M+H)^+$. $^{13}C$ NMR ($CDCl_3$): δ182.6, 182.2, 174.8, 169.8, 156.1, 141.7, 122.0, 99.5, 81.8, 81.2, 78.9, 77.9, 77.8, 76.7, 75.9, 75.5, 74.1, 71.6, 68.8, 65.6, 63.1, 43.5, 40.6, 40.5, 38.2, 36.5, 35.4, 31.5, 30.9, 28.1, 27.9, 23.0, 22.6, 21.4, 21.1, 19.9, 19.5, 16.9, 15.8, 14.4, 14.1, 11.6, 7.6.

Step 1b. Compound (1.5) of Scheme (1): $n=m=0$, $R_{10}=R_{11}=H$, $R_p=Ac$, $PG=Boc$, $U=OH$, $V=H$, $X=CH_3$, $Y=H$ To a solution of the compound from Step 1a (5.0 g, 5.94 mmol) in acetone (30 mL) and water (30 mL) was added $NaIO_4$ (3.16 g, 14.77 mmol) and $OsO_4$ (4% in water, 6 mL, 0.96 mmol) at room temperature. The resulting mixture was stirred for 2 hours. The reaction mixture was quenched with $NaHSO_3$ at 0° C. and stirred for 20 min. The resulting mixture was extracted with $CH_2Cl_2$ (50 mL×3). The combined organic phases were washed with brine, dried ($Na_2SO_4$), filtered and concentrated to give 4.90 g of the crude mixture, which was purified by flash chromatography (silica gel, acetone/hexane=1/3) to afford 1.55 g (31%) of the title compound. MS (ESI) m/z=844 $(M+H)^+$. $^{13}C$ NMR ($CDCl_3$): δ205.0, 182.5, 181.3, 175.5, 169.9, 156.0, 99.4, 82.0, 81.9, 80.7, 79.7, 78.4, 77.6, 75.8, 75.4, 71.6, 69.0, 63.1, 43.9, 40.6, 40.1, 38.6, 36.6, 36.0, 30.9, 28.2, 22.7, 21.4, 21.1, 19.9, 19.4, 16.8, 15.7, 14.6, 11.2, 7.6.

Step 1c. Compound (1.6) of Scheme (1): $n=m=0$, $R_{10}=R_{11}=H$, $R_p=Ac$, $U=OH$, $V=H$, $X=CH_3$, $Y=H$ To a solution of the compound from Step 1b (1.40 g, 1.66 mmol) in $CH_2Cl_2$ (12 mL) was added TFA (6 mL) dropwise during 5 minutes period at 0° C. The resulting mixture was kept at 0° C. for 2 hours. The mixture was neutralized carefully with cold saturated $NaHCO_3$ at 0° C. to pH 8.5. The resulting mixture was extracted with $CH_2Cl_2$ (50 mL×3). The combined organic phases were washed with brine, dried ($Na_2SO_4$), filtered and concentrated to provide crude product (1.09 g). The crude residue was purified by flash chromatography (silica gel, acetone/hexane=1/3 to 1/1) to afford 623 mg (52%) of the title compound as a mixture of bridged oximes (E/Z=1:1). The mixture was separated by HPLC (50% $CH_3CN$ in 20 mM $NH_4HCO_3$ aqueous buffer) to afford 107 mg of Z-isomer (MS (ESI) m/z=726 $(M+H)^+$) and 135 mg of E-isomer. MS (ESI) m/z=726 $(M+H)^+$.

Example 2

Compound of Formula (V): $R_{10}=R_p=H$, $R_p=H$, $X=CH_3$, $Y=H$

Step 2a. Compound of Formula (1.6): $n=m=0$, $R_{10}=R_p=H$, $R_p=Ac$, U and V are taken together to form a carbonyl group, $X=CH_3$, $Y=H$ To a solution of compound from Example 1, Step 1c (Z-isomer) (105 mg, 0.14 mmol) in $CH_2Cl_2$ (5 mL) was added AcOH (0.008 mL, 0.14 mmol), followed by addition of Dess-Martin periodinane (123 mg, 0.28 mmol) at room temperature. The resulting mixture was stirred at room temperature for 2 hours. The reaction mixture was diluted with $CH_2Cl_2$, washed with cold 1N NaOH (15 mL×2) and brine, dried ($Na_2SO_4$), filtered and filtrate was concentrated to give 103 mg (100%) of the title compound. MS (ESI) m/z=724 $(M+H)^+$.

Step 2b. Compound of Formula (V): $R_{10}=R_p=H$, $R_p=H$, $X=CH_3$, $Y=H$

A solution of compound from Step 2a (103 mg, 0.14 mmol) in MeOH (2 mL) was stirred at room temperature for overnight. MeOH was removed under reduced pressure to afford 97 mg (100%) of the title compound. MS (ESI) m/z=682 $(M+H)^+$. $^{13}C$ NMR ($CDCl_3$): δ205.3, 181.9, 176.2, 170.1, 154.4, 102.8, 79.5, 78.5, 78.2, 77.8, 75.7, 73.2, 70.8, 70.2, 69.6, 65.9, 54.8, 51.2, 46.3, 41.0, 40.2, 39.5, 39.4, 28.2, 22.3, 21.2, 20.6, 17.0, 15.0, 14.0, 13.9, 11.0.

Example 3

Compound of Formula (V): $R_{10}=R_{11}=H$, $R_p=H$, $X=CH_3$, $Y=H$

Step 3a. Compound of Formula (1.6): n=m=0, $R_{10}=R_p=H$, $R_p=Ac$, U and V are taken together to form a carbonyl group, $X=CH_3$, $Y=H$ To a solution of compound from Example 1, Step 1c (E-isomer) (135 mg, 0.19 mmol) in $CH_2Cl_2$ (5 mL) was added AcOH (0.016 mL), followed by addition of Dess-Martin periodinane (159 mg, 0.38 mmol) at room temperature. The resulting mixture was stirred at room temperature for 2 hours. The reaction mixture was diluted with $CH_2Cl_2$, washed with cold 1N NaOH (15 mL×2) and brine, dried ($Na_2SO_4$), filtered and filtrate was concentrated to give 132 mg (100%) of the title compound. MS (ESI) m/z=724 (M+H)$^+$.

Step 3b. Compound of Formula (V): $R_{10}=R_{11}=H$, $R_p=H$, $X=CH_3$, $Y=H$

A solution of compound from Step 3a (132 mg, 0.19 mmol) in MeOH (2 mL) was stirred at room temperature for overnight. MeOH was removed under reduced pressure and the residue was purified by flash chromatography (silica gel, acetone/hexane=1/1) to afford 109 mg (88%) of the title compound. MS (ESI) m/z=682 (M+H)$^+$. $^{13}$C NMR (CDCl$_3$): δ203.7, 182.7, 177.0, 169.3, 158.6, 104.2, 83.5, 81.3, 78.4, 75.5, 75.3, 73.2, 70.3, 69.6, 65.8, 63.1, 51.5, 47.9, 40.2, 39.8, 37.8, 36.9, 28.0, 25.2, 22.4, 21.3, 21.0, 16.5, 15.3, 14.0, 13.7, 10.9.

Example 4

Compound of Formula (IV): $R_{10}=Ph$, $R_{11}=H$, $R_p=Ac$, U=OH, V=H, $X=CH_3$, Y=H Step 4a. Preparation of: (1,3-Dioxo-1,3-dihydro-isoindol-2-yloxy)-phenyl-acetic acid benzyl ester To a solution of benzyl-2-hydroxy-2-phenylacetate (2.42 g, 10 mmol), N-hydroxyphthalimide (1.96 g, 12 mmol) and PPh3 (3.4 g, 13 mmol) in $CH_2Cl_2$ (30 mL) was added DIAD (2.63 g, 13 mmol) at −20° C. The resulting mixture was stirred at −20° C. for 1 hour. The reaction mixture was concentrated and purified by flash chromatography (silica gel, Hexanes/$CH_2Cl_2$=1/3) giving 3.8 g (98%) of the title compound.

Step 4b. Preparation of: Aminooxy-phenyl-acetic acid benzyl ester

A solution of the compound from Step 4a (3.8 g, 9.8 mmol) and hydrazine (0.64 mL, 20 mmol) in EtOH (30 mL) was stirred at room temperature for 2 hours. The reaction mixture was filtered. The filtrate was concentrated and the residue was dissolved in EtOAc. The organic phase was washed with brine, dried ($Na_2SO_4$), filtered and solvent was reduced under reduced pressure giving 2.4 g (95%) of the title compound, which was used without additional purification.

Step 4c. Preparation of: N-Boc-aminooxy-phenyl-acetic acid benzyl ester

A mixture of the compound from Step 4b (2.4 g, 9.3 mmol) and Boc$_2$O (4.37 g, 20 mmol) in acetonitrile (20 mL) was heated at 70° C. for 3 hours. The reaction mixture was concentrated and the residue was dissolved in EtOAc (100 mL). The organic phase was washed with saturated NaHCO$_3$ and brine, dried ($Na_2SO_4$) and filtered. The solvent was removed under reduced pressure. The residue was purified by flash chromatography (silica gel, Hexanes/Et$_2$O=4/1 to 2/1) giving 2.8 g (84%) of the title compound.

Step 4d. Preparation of: N-Boc-aminooxy-phenyl-acetic acid

A mixture of the compound from Step 4c (2.8 g, 7.8 mmol) and 1 N NaOH (15 mL, 15 mmol) in MeOH (30 mL) was stirred at room temperature for 3 hours. The reaction mixture was neutralized by 2 N HCl to pH ~2. The resulting mixture was extracted with EtOAc (50 mL×3). The combined organic phases were washed with NH$_4$Cl and brine, dried ($Na_2SO_4$) and filtered. The filtrate was concentrated and residue was purified by flash chromatography (silica gel, EtOAc/$CH_2Cl_2$=1/4) giving 0.6 g (29%) of the title compound.

Step 4e. Compound (1.4) of Scheme (1): n=m=0, $R_{10}=Ph$, $R_p=H$, $R_p=Ac$, PG=Boc, U=OH, V=H, $X=CH_3$, Y=H To a mixture of (1.1) of Scheme 1 (where $R_p=Ac$, U=OH, $X=CH_3$, and V and Y are hydrogen) (1.0 g, 1.5 mmol) and compound from Step 4d (560 mg, 2 mmol) in $CH_2Cl_2$ (30 mL) was added EDC.HCl (784 mg, 4 mmol) and DIPEA (1.1 mL, 6 mmol) at 0° C. The resulting mixture was stirred at room temperature for 5 hours. Reaction mixture was diluted with EtOAc and washed with saturated NaHCO$_3$ and brine. The organic phase was dried ($Na_2SO_4$), filtered and solvent was removed under reduced pressure. The residue was purified by flash chromatography (silica gel, Hexanes/Acetone=4/1 to 1/1) giving 700 mg (51%) of the title compound. (MS (ESI) m/z=918 (M+H)$^+$.

Step 4f. Compound (1.5) of Scheme (1): n=m=0, $R_{10}=Ph$, $R_{11}=H$, $R_p=Ac$, PG=Boc, U=OH, V=H, $X=CH_3$, Y=H To a solution of compound from Step 4e (700 mg, 0.76 mmol) in acetone (10 mL) and H$_2$O (5 mL) was added OsO$_4$ (4% in H$_2$O, 2 mL) at room temperature. The resulting mixture was stirred at room temperature for 5 min, followed by addition of NaIO$_4$ (428 mg, 2 mmol). The reaction mixture was stirred at room temperature for 3 hours. The reaction mixture was quenched with NaHSO$_3$ and extracted with EtOAc (30 mL×3). The combined organic phases were washed with NaHCO$_3$, dried ($Na_2SO_4$) and filtered. The organic solvent was removed under reduced pressure. The residue was purified by flash chromatography (silica gel, Acetone/Hexanes=2/1 to 1/1) giving 400 mg (57%) of the title compound. (MS (ESI) m/z=920 (M+H)$^+$.

Step 4g. Compound of Formula (IV): $R_{10}=Ph$, $R_{11}=H$, $R_p=Ac$, U=OH, V=H, $X=CH_3$, Y=H (or Compound (1.6) of Scheme (1): n=m=0, $R_{10}=Ph$, $R_{11}=H$, $R_p=Ac$, U=OH, V=H, $X=CH_3$, Y=H)

To a solution of the compound from Step 4f (400 mg, 0.43 mmol) in $CH_2Cl_2$ (4 mL) was added TFA (2 mL) at 0° C. The resulting mixture was stirred at 0° C. for 2 hours. The reaction mixture was poured into saturated NaHCO$_3$ (20 mL) at 0° C. The mixture was extracted with EtOAc (20 mL) and organic phase was washed with Na$_2$CO$_3$ (20 mL), dried ($Na_2SO_4$) and filtered. The filtrate was concentrated and the residue was purified by flash chromatography (silica gel, Hexanes/Acetone=2/1 to 1/1) giving 150 mg (43%) of the title compound as one major isomer. (MS (ESI) m/z=802 (M+H)$^+$.

Example 5

Compound of formula (V): $R_{10}$=Ph, $R_{11}$=H, $R_p$=H, X=$CH_3$, Y=H

Step 5a. Compound of formula (V): $R_{10}$=Ph, $R_{11}$=H, $R_p$=Ac, X=$CH_3$, Y=H A mixture of compound from Step 4g (150 mg, 0.19 mmol), HOAc (200 mL) and Dess-Martin periodinane (220 mg, 0.5 mmol) in $CH_2Cl_2$ (5 mL) was stirred at room temperature for 2 hours. The reaction mixture was quenched with saturated $NaHCO_3$ and resulting mixture was washed with 0.5 N NaOH. The organic phase was dried ($Na_2SO_4$), filtered and filtrate was concentrated. The residue was purified by flash chromatography (silica gel, hexanes/acetone) giving 120 mg of the title compound, which was further purified by HPLC giving 26 mg of pure title compound. (MS (ESI) m/z=800 (M+H)$^+$. $^{13}$C NMR(CDCl$_3$): δ204.0, 183.3, 177.7, 170.0, 169.6, 159.0, 135.9, 129.2, 128.8, 128.3, 102.2, 86.6, 81.7, 78.9, 75.9, 75.4, 71.7, 69.5, 66.2, 63.7, 63.5, 51.8, 47.6, 40.8, 39.5, 38.3, 36.7, 30.5, 29.9, 25.5, 22.8, 21.7, 21.2, 17.1, 15.3, 14.2, 13.6, 11.3.

Step 5b. Compound of formula (V): $R_{10}$=Ph, $R_{11}$=H, $R_p$=H, X=$CH_3$, Y=H A solution of compound from Step 5a (26 mg, 0.0325 mmol) in MeOH (10 mL) was heated at 60° C. until the reaction was done. Solvent was removed under reduced pressure giving 24 mg (100%) of the title compound. (MS (ESI) m/z=758.5 (M+H)$^+$. $^{13}$C NMR (CDCl$_3$): δ204.1, 183.4, 177.8, 169.7, 159.1, 135.9, 129.2, 128.8, 128.3, 104.4, 86.5, 83.8, 81.6, 78.7, 75.9, 75.4, 70.6, 69.9, 66.2, 66.1, 63.5, 51.8, 48.1, 40.5, 39.6, 38.3, 29.9, 28.5, 25.7, 22.8, 21.7, 21.4, 17.0, 15.5, 14.4, 13.7, 11.3.

Example 6

Compounds of Formula (IV): $R_{10}$=Bn, $R_{11}$=H, $R_p$=Ac, U=OH, V=H, X=$CH_3$, Y=H and $R_{10}$=H, $R_{11}$=Bn, $R_p$=Ac, U=OH, V=H, X=$CH_3$, Y=H

Step 6a. Compound of Formula: 2-Hydroxy-3-phenyl-propionic acid benzyl ester To a solution of DL-Phenyllactic acid (5.0 g, 30.09 mmol) in DMF (30 mL) was added $Cs_2CO_3$ (10.79 g, 33.11 mmol) in portions during 10 minutes period at room temperature. The resulting mixture was stirred for 15 min at room temperature, followed by the addition of benzyl bromide (3.57 mL, 30.09 mmol). The resulting mixture was stirred at room temperature overnight. The reaction mixture was diluted with EtOAc (300 mL), washed with saturated $NaHCO_3$, water (100×2) and brine, dried ($Na_2SO_4$) and filtered. The filtrate was concentrated to give 7.20 g (89%) of the title compound.

Step 6b. Preparation of: 2-(1,3-Dioxo-1,3-dihydro-isoindol-2-yloxy)-3-phenyl-propionic acid benzyl ester To a mixture of compound from Step 6a (7.00 g, 27.2 mmol), N-hydroxyphthalimide (5.35 g, 32.80 mmol) and PPh$_3$ (9.26 g, 35.30 mmol) in $CH_2Cl_2$ (55 mL) was added diisopropyl azodicarboxylate (6.86 mL, 35.38 mmol) during 10 minutes period at –20° C. The resulting mixture was stirred at –20° C. for 2 hours. The solvent was removed under reduced pressure. The residue was purified by flash chromatography (silica gel, $CH_2Cl_2$/hexane=1/2) to afford 10.65 g (99%) of the title compound.

Step 6c. Preparation of: 2-Aminooxy-3-phenyl-propionic acid benzyl ester

To a solution of the compound from Step 6b (10.00 g, 24.94 mmol) in EtOH (150 mL) was added hydrazine monohydrate (2.50 mL, 49.88 mmol) at room temperature. The resulting mixture was stirred for 1 hour at room temperature, diluted with EtOAc (450 mL), washed with saturated $NaHCO_3$, water (300 mL×2) and brine, dried ($Na_2SO_4$), filtered and concentrated to afford 6.73 g of crude product, which was purified by flash chromatography (silica gel, $CH_2Cl_2$/Hexane=15/1) to provide 5.37 g (80%) of the title compound. $^{13}$C NMR (CDCl$_3$): δ171.9, 136.6, 135.4, 129.3, 129.2, 129.1, 128.4, 128.3, 128.2, 128.1, 128.0, 126.6, 83.8, 66.4, 37.3.

Step 6d. Preparation of: N-Boc-2-Aminooxy-3-phenyl-propionic acid benzyl ester To a solution of the compound from Step 6c (4.70 g, 17.34 mmol) in $CH_3CN$ (30 mL) was added Boc$_2$O (7.34 g, 33.98 mmol) at room temperature. The resulting mixture was heated at 80° C. for 3 hours. Solvent was removed under reduced pressure. The residue was purified by flash chromatography (silica gel, Et$_2$O/Hexane=1/10) to afford 5.48 g (87%) of the title compound.

Step 6e. Preparation of: N-Boc-2-Aminooxy-3-phenyl-propionic acid

A mixture of the compound from Step 6d (4.00 g, 10.78 mmol) and 2 N NaOH (20 mL) in MeOH (100 mL) were stirred at room temperature for 2 hours. Solvent was removed under reduced pressure. The residue was acidified with 2 N HCl to pH 2. The resulting mixture was extracted with EtOAc (200 mL×3), dried ($Na_2SO_4$), filtered and concentrated to give 3.72 g of the crude product, which was purified by flash chromatography (silica gel, $CH_2Cl_2$ then 4% MeOH in $CH_2Cl_2$) to afford 2.48 g (83%) of the title compound.

Step 6f. Compound (1.4) of Scheme (1): n=m=0, $R_{10}$=Bn, $R_{11}$=H, $R_p$=Ac, PG=Boc, U=OH, V=H, X=$CH_3$, Y=H and Compound (1.4) of Scheme (1): n=m=0, $R_{10}$=H, $R_{11}$=Bn, $R_p$=Ac, PG=Boc, U=OH, V=H, X=$CH_3$, Y=H(mixture)

To a solution of compound (1.1) of Scheme 1 (where $R_p$=Ac, U=OH, X=$CH_3$, and V and Y are hydrogen) (3.0 g, 4.50 mmol) and compound from Step 6e (2.48 g, 8.82 mmol) in $CH_2Cl_2$ (30 mL) was added EDC.HCl (2.32 g, 15 mmol), followed by addition of diisopropylethyl amine (6.30 mL, 36.17 mmol) at room temperature. The resulting mixture was stirred for 20 h. The mixture was diluted with $CH_2Cl_2$ (250 mL), washed with saturated $NaHCO_3$ (200 mL×2) and brine, dried ($Na_2SO_4$) and filtered. The filtrate was concentrated to give 3.38 g of the crude mixture, which was purified by flash chromatography (silica gel, EtOAc/Hexane=4/1) to afford 2.58 g (63%) of the title compound. MS (ESI) m/z=932 (M+H)$^+$.

Step 6g. Compound (1.5) of Scheme (1): n=m=0, $R_{10}$=Bn, $R_{11}$=H, $R_p$=Ac, PG=Boc, U=OH, V=H, X=$CH_3$, Y=H and Compound(1.5) of Scheme(1): n=m=0, $R_{10}$=H, $R_{11}$=Bn, $R_p$=Ac, PG=Boc, U=OH, V=H, X=$CH_3$, Y=H (mixture)

To a solution of the compound from Step 6f (2.58 g, 2.77 mmol) in acetone (35 mL) and water (17 mL) was added NaIO$_4$ (1.55 g, 7.26 mmol) followed by addition of OsO$_4$ (4% in water, 2.88 mL, 0.46 mmol) at room temperature. The resulting mixture was stirred for 2 hours. The reaction mixture was quenched with saturated $Na_2SO_3$, extracted with EtOAc (100 mL×3). The combined organic phases were washed with brine, dried ($Na_2SO_4$) and filtered. The filtrate was concentrated to provide 2.48 g of the crude product, which was purified by flash chromatography (silica gel, acetone/hexanes=1/2 then 1/1) to afford 1.83 g (71%) of the title compound. MS (ESI) m/z=934 (M+H)$^+$.

Step 6h. Compound (1.6) of Scheme (1): n=m=0, $R_{10}$=Bn, $R_{11}$=H, $R_p$=Ac, U=OH, V=H, X=CH$_3$, Y=H and Compound (1.6) of Scheme (1): n=m=0, $R_{10}$=H, $R_{11}$=Bn, $R_p$=Ac, U=OH, V=H, X=CH$_3$, Y=H To a solution of compound from Step 6g (1.80 g, 1.93 mmol) in CH$_2$Cl$_2$ (12 mL) was added TFA (6 mL) during 5 minutes period at 0° C. The resulting mixture was stirred for 2 hours at 0° C. The reaction mixture was carefully neutralized with cold saturated NaHCO$_3$ at 0° C. to pH 8.5. The resulting mixture was extracted with EtOAc (50 mL×3). The combined organic phases were washed with brine, dried (Na$_2$SO$_4$) and filtered. The filtrate was concentrated to give 1.10 g of the crude product, which was purified by flash chromatography (silica gel, acetone/hexanes=1/2) to afford 987 mg (70%) of the title compound as a mixture of bridged oximes E/Z=1/1. Part of this mixture (380 mg) was separated by HPLC (60% CH$_3$CN in 20 mM NH$_4$HCO$_3$ aqueous buffer) to provide 80 mg of E-(R)-isomer: MS (ESI) m/z=816 (M+H)$^+$; $^{13}$C NMR (CDCl3): δ183.1, 175.4, 169.7, 158.4, 137.3, 129.4, 128.1, 126.5, 100.2, 84.8, 84.3, 82.2, 78.3, 77.3, 75.9, 71.2, 68.9, 65.9, 64.1, 63.1, 44.1, 40.6, 40.4, 38.5, 38.4, 36.6, 35.7, 31.0, 26.2, 22.5, 21.4, 21.0, 20.1, 16.7, 14.9, 14.0, 10.7, 7.6) and 60 mg of Z- (S)-isomer. MS (ESI) m/z=816 (M+H)$^+$. $^{13}$C NMR(CDCl$_3$): δ182.7, 176.7, 176.0, 169.8, 153.2, 137.6, 129.7, 129.4, 128.3, 128.2, 126.5, 99.6, 83.4, 79.1, 78.9, 78.7, 77.5, 75.7, 71.5, 70.9, 68.9, 63.1, 54.8, 44.1, 41.6, 40.6, 40.2, 36.6, 35.9, 35.7, 34.8, 30.9, 22.1, 21.4, 21.2, 21.1, 19.5, 16.8, 15.5, 14.9, 10.7, 7.5.

Example 7

Compound of Formula (V): $R_{10}$=H, $R_{11}$=Bn, $R_p$=H, X=CH$_3$, Y=H

Step 7a. Compound of Formula (V): $R_{10}$=H, $R_{11}$=Bn, $R_p$=Ac, X=CH$_3$, Y=H To a solution of the compound from Example 6, Step 6h (Z (S)-isomer) (60 mg, 0.074 mmol) in CH$_2$Cl$_2$ (2 mL) was added AcOH (0.006 mL, 2 eq), followed by addition of Dess-Martin periodinane (62 mg, 0.15 mmol) at room temperature. The resulting mixture was stirred at room temperature for 2 hours. The reaction mixture was diluted with CH$_2$Cl$_2$, washed with cold 1N NaOH (4 mL×2) and brine, dried (Na$_2$SO$_4$), filtered and filtrate was concentrated to give 54 mg (90%) of the title compound. MS (ESI) m/z=814 (M+H)$^+$.

Step 7b. Compound of Formula (V): $R_{10}$=H, $R_{11}$=Bn, $R_p$=H, X=CH$_3$, Y=H A solution of the compound from Step 7a (54 mg, 0.066 mmol) in MeOH (1 mL) was refluxed for 3 hours. The solvent was removed under reduced pressure and the residue was purified by flash chromatography (silica gel, acetone/hexane=1/2 then 1/1) to afford 47 mg (93%) of the title compound. MS (ESI) m/z=772 (M+H)$^+$. $^{13}$C NMR (CDCl3): δ6205.3, 182.6, 176.3, 170.1, 153.1, 137.6, 129.4, 128.3, 126.5, 102.9, 83.6, 79.2, 78.5, 78.3, 77.9, 75.8, 71.0, 70.3, 69.6, 65.9, 54.8, 51.2, 46.3, 41.1, 40.2, 36.6, 36.4, 34.9, 28.2, 22.3, 21.3, 21.2, 20.3, 17.0, 15.0, 14.0, 13.8, 11.0.

Example 8

Compound of Formula (V): $R_{10}$=Bn, $R_p$=H, $R_p$=H, X=CH$_3$, Y=H

Step 8a. Compound of Formula (V): $R_{10}$=Bn, $R_p$=H, $R_p$=Ac, X=CH$_3$, Y=H

To a solution of compound from Example 6, Step 6h (E-(R)-isomer) (80 mg, 0.098 mmol) in CH$_2$Cl$_2$ (2.6 mL) was added AcOH (0.008 mL, 2 eq), followed by addition of Dess-Martin periodinane (81 mg, 2 eq) at room temperature. The resulting mixture was stirred at room temperature for 2 hours. The reaction mixture was diluted with CH$_2$Cl$_2$, washed with cold 1N NaOH (4 mL×2) and brine, dried (Na$_2$SO$_4$), filtered and filtrate was concentrated to afford 78 mg (100%) of the title compound. MS (ESI) m/z=814 (M+H)$^+$. $^{13}$C NMR (CDCl3): δ203.7, 184.2, 175.8, 169.7, 169.3, 157.9, 137.4, 129.3, 128.2, 126.5, 101.9, 85.0, 83.0, 81.2, 78.6, 75.5, 75.0, 71.4, 69.2, 65.8, 63.3, 63.2, 51.5, 47.3, 40.5, 39.6, 38.3, 37.8, 36.4, 30.2, 25.1, 22.5, 21.3, 20.9, 16.8, 15.0, 13.8, 13.3, 11.0.

Step 8b. Compound of Formula (V): $R_{10}$=Bn, $R_{11}$=H, $R_p$=H, X=CH$_3$, Y=H A solution of the compound from Step 8a (78 mg, 0.096 mmol) in MeOH (1.5 mL) was refluxed for 3 hours. The solvent was removed under reduced pressure to afford 74 mg (100%) of the title compound. MS (ESI) m/z=772 (M+H)$^+$. $^{13}$C NMR (CDCl3): δ203.8, 184.4, 175.9, 169.3, 158.1, 137.4, 129.3, 128.2, 126.5, 104.1, 85.0, 83.5, 81.2, 78.4, 75.6, 74.9, 70.3, 69.6, 65.8, 63.2, 51.5, 47.8, 40.2, 39.8, 38.4, 37.8, 36.8, 31.5, 28.1, 25.3, 22.6, 22.5, 21.3, 21.1, 16.6, 15.2, 14.1, 13.3, 11.0.

Example 9

Compounds of Formula (IV): $R_{10}$=CH$_2$CH$_2$Ph, $R_{11}$=H, $R_p$=Ac, U=OH, V=H, X=CH$_3$, Y=H and $R_{10}$=H, $R_1$=Bn, $R_p$=Ac, U=OH, V=H, X=CH$_3$, Y=H Step 9a. Compound of Formula: 2-Methanesulfonyloxy-4-phenyl-butyric acid ethyl ester To a solution of ethyl-2-hydroxy-4-phenylbutyrate (2.08 g, 10 mmol) in CH$_2$Cl$_2$ (20 mL) was added triethylamine (2.1 mL, 15 mmol) and Ms$_2$O (1.92 g, 11 mmol) at 0° C. The resulting reaction mixture was stirred at room temperature for 15 min. DMAP (50 mg) was added to the reaction mixture. The reaction mixture was stirred at room temperature for 4 hours. The reaction was quenched with saturated NaHCO$_3$. The resulting mixture was extracted with CH$_2$Cl$_2$ (3×50 mL). The combined organic phases were dried (Na$_2$SO$_4$), filtered and CH$_2$Cl$_2$ was removed under reduced pressure. The residue was purified by flash chromatography (CH$_2$Cl$_2$), giving 2.7 g (94%) of the title compound. $^{13}$C NMR (CDCl3): 6169.3, 140.0, 128.9, 128.8, 126.7, 62.3, 52.8, 39.5, 33.9, 31.2, 14.3.

Step 9b. Preparation of: N-Boc-2-Aminooxy-4-phenyl-butyric acid ethyl ester

To a solution of BocNHOH (958 mg, 7.2 mmol) in DMF (15 mL) was added NaH (60% in mineral oil, 320 mg, 8 mmol) at 0° C. The resulting mixture was stirred at 0° C. for 15 min. The compound from Step 9a (1.81 g, 6 mmol) was added to the mixture at 0° C. The resulting mixture was stirred at room temperature for 2 hours. The reaction mixture was quenched with saturated NH$_4$Cl and extracted with EtOAc (3×15 mL), dried (Na$_2$SO$_4$) and filtered. The organic solvent was removed under reduced pressure and residue was purified by flash chromatography (Hexanes/EtOAc=3/1), giving 1 g (50%) of the title compound. $^{13}$C NMR (CDCl3): δ17172.0, 156.6, 141.3, 128.8, 128.7, 126.3, 83.3, 82.2, 61.5, 33.0, 31.7, 28.5, 14.5.

Step 9c. Preparation of: N-Boc-2-Aminooxy-4-phenyl-butyric acid

A solution of the compound from Step 9b (950 mg, 3 mmol) in MeOH (20 mL) and 2 N NaOH (4 mL) were stirred at room temperature for 3 hours. The mixture was concentrated under reduced pressure, acidified to pH ~2.0 with 2 N HCl. The resulting mixture was extracted with EtOAc (3×50 mL), dried (Na$_2$SO$_4$) and filtered. The solvent was removed under reduced pressure and residue was purified by flash chromatography (CH$_2$Cl$_2$; CH$_2$Cl$_2$/MeOH=10/1) giving 900 mg (86%) of the title compound.

Step 9d. Compound (1.4) of Scheme 1: n=m=0, R$_{10}$=CH$_2$CH$_2$Ph, R$_{11}$=H, R$_p$=Ac, PG=Boc, U=OH, V=H, X=CH$_3$, Y=H To a solution of (1.1) of Scheme 1 (where R$_p$=Ac, U=OH, X=CH$_3$ and V and Y are hydrogen) (1.0 g, 1.5 mmol) and the compound from Step 9c (900 mg, 2.8 mmol) in CH$_2$Cl$_2$ (30 mL) was added EDC.HCl (775 mg, 5 mmol) and DIPEA (2.1 mL, 12 mmol) at 0° C. The resulting mixture was stirred at room temperature for 5 hours. Reaction mixture was diluted with EtOAc and washed with saturated NaHCO$_3$ and brine. The organic phase was dried (Na$_2$SO$_4$), filtered and solvent was removed under reduced pressure. The residue was purified by flash chromatography on silica gel (Hexanes/Acetone=4/1 to 1/1) giving 800 mg (57%) of the title compound. MS(ESI) m/z=946.5 (M+H)$^+$ Step 9e. Compound (1.5) of Scheme 1: n=m=0, R$_{10}$=CH$_2$CH$_2$Ph, R$_{11}$=H, R$_p$=Ac, PG=Boc, U=OH, V=H, X=CH$_3$, Y=H To a solution of the compound from Step 9d (700 mg, 0.74 mmol) in acetone (10 mL) and H$_2$O (5 mL) was added OsO$_4$ (4% in H$_2$O; 0.8 mL) and NaIO$_4$ (430 mg, 2 mmol). The reaction mixture was stirred at room temperature for 2 hours. The reaction was quenched with NaHCO$_3$ and Na$_2$S$_2$O$_3$. The resulting mixture was extracted with EtOAc (3×20 mL). The combined organic phases were dried (Na$_2$SO$_4$), filtered and concentrated under reduced pressure giving 700 mg (100%) of the title compound (crude). MS(ESI) m/z=948.5(M+H)$^+$ Step 9f. Compound of Formula (IV): R$_{10}$=CH$_2$CH$_2$Ph, R$_{11}$ H, R$_p$=Ac, U=OH, V=H, X=CH$_3$, Y=H To a solution of the compound from Step 9e (600 mg, 0.6 mmol) in CH$_2$Cl$_2$ (6 mL) was added TFA (3 mL) at 0° C. The reaction mixture was stirred at 0° C. for 1 hour. The reaction mixture was poured to saturated NaHCO$_3$ at 0° C. The resulting mixture was extracted with EtOAc (3×10 mL). The combined organic phases were washed with saturated NaHCO$_3$ and brine, dried (Na$_2$SO$_4$), filtered and concentrated under reduced pressure. The residue was purified by flash chromatography (silica gel, Hexanes/Acetone), giving 210 mg of the title compound as a bridged oxime mixture in a ratio E/Z=1/7. HPLC purification gave 20 mg of Z isomer of the title compound. MS (ESI) m/z=830 (M+H)$^+$ Example 10

Compound of Formula (V): R$_{10}$=CH$_2$CH$_2$Ph, R$_{11}$=H, R$_p$=H, X=CH$_3$, Y=H Step 10a. Compound of Formula (V): R$_{10}$=CH$_2$CH$_2$Ph, R$_{11}$=H, R$_p$=Ac, X=CH$_3$, Y=H To a solution of the compound from Example 9, Step 9f (20 mg, 0.024 mmol) in CH$_2$Cl$_2$ (1 mL) was added acetic acid (3 mg, 0.048 mmol), followed by addition of Dess-Martin reagent (20 mg, 0.048 mmol) at room temperature. The resulting mixture was stirred at room temperature for two hours. The reaction mixture was diluted with CH$_2$Cl$_2$, washed with 1 N NaOH (2×2 mL), saturated NaHCO$_3$ and brine. The organic phase was dried (Na$_2$SO$_4$), filtered and concentrated under reduced pressure to give 5 mg (25%) of the title compound. MS (ESI) m/z=828 (M+H)$^+$.

Step 10b. Compound of Formula (V): R$_{10}$=CH$_2$CH$_2$Ph, R$_{11}$=H, R$_p$=H, X=CH$_3$, Y =H A solution of the compound from Step 10a (5 mg) in MeOH (2 mL) was heated at 55° C. for 4 hours. The solvent was removed under reduced pressure giving 3.6 mg (63%) of the title compound. MS (ESI) m/z=787 (M+H)$^+$.

What is claimed is:

1. A compound represented by the formula (I)

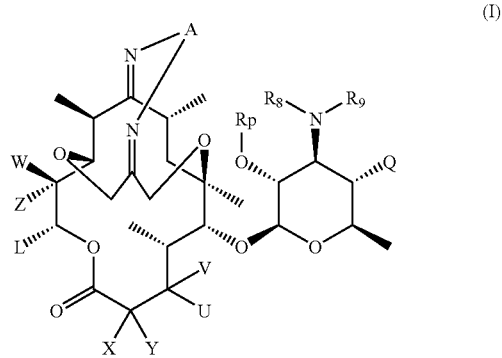

or the racemates, enantiomers, diastereomers, geometric isomers, tautomers, solvates, pharmaceutically acceptable salts and esters thereof, wherein A is -J- where J is absent or is selected from the group consisting of: O, OC(O), C(O), S(O)$_n$, NH, NH(CO), NH(CO)NH, or NHS(O)$_n$ where n is 0, 1, or 2 and R$_1$ is absent or is a substituted or unsubstituted —C$_1$-C$_8$ alkylene, —C$_2$-C$_8$ alkenylene or —C$_2$-C$_8$ alkynylene optionally containing one or more heteroatoms selected from O, S or N;

L is:
a) —CH$_2$CH$_3$;
b) —CH(OH)CH$_3$; or
c) —R$_2$, where R$_2$ is:
  i. —C$_{1-C6}$ alkyl containing 0, 1, 2, or 3 heteroatoms selected from O, S or N, optionally substituted with one or more substituents selected from halogen, aryl, substituted aryl, heteroaryl, substituted heteroaryl;
  ii. —C$_2$-C$_6$ alkenyl containing 0, 1, 2, or 3 heteroatoms selected from O, S or N, optionally substituted with one or more substituents selected from halogen, aryl, substituted aryl, heteroaryl, or substituted heteroaryl; or
  iii. —C$_1$-C$_6$ alkynyl containing 0, 1, 2, or 3 heteroatoms selected from O, S or N, optionally substituted with one or more substituents selected from halogen, aryl, substituted aryl, heteroaryl, or substituted heteroaryl;

Q is:
a) hydrogen;
b) protected hydroxyl; or c) —OR$_3$, where R$_3$ is selected from the group consisting of:
i. hydrogen;
ii. aryl; substituted aryl; heteroaryl; substituted heteroaryl;
iii. —R$_2$; or
iv. C$_3$-C$_{12}$ cycloalkyl containing 0, 1, 2, or 3 heteroatoms selected from O, S or N, optionally substituted with one or more substituents selected from halogen, aryl, substituted aryl, heteroaryl, or substituted heteroaryl;

One U or V is hydrogen and the other is independently:
a) hydrogen;
b) hydroxyl;
c) protected hydroxyl;
d) —R$_2$;
e) —OR$_2$;
f) —C(O)R$_2$;
g) —OC(O)R$_2$;
h) —S(O)$_n$R$_2$; or
i)

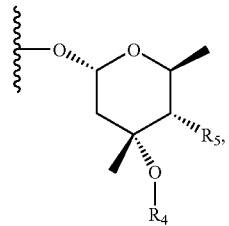

where R$_4$ is selected from the group consisting of hydrogen or/and methyl and R$_5$ is:
i. hydrogen;
ii. hydroxyl or hydroxyl protecting group;
iii. —R$_2$; or
iv. —OR$_2$;

Alternatively, U and V taken together with the carbon atom to which they are attached to form a carbonyl group;

W is:
a) hydroxyl;
b) —NR$_6$R$_7$, where each R$_6$ and R$_7$ are hydrogen or R$_2$ or R$_6$ and R$_7$ taken together with the nitrogen atom to which they are attached to form a substituted or unsubstituted heterocyclic ring;
c) —O—R$_2$; or
d) —OC(O)NR$_6$R$_7$;

Z is:
a) hydrogen;
b) —N$_3$;
c) —CN;
d) —NO$_2$;
e) —CONH$_2$;
f) —COOH;
g) —CHO;
h) —R$_2$;
i) —COOR$_2$;
j) —C(O)R$_2$; or
k) —C(O)NR$_6$R$_7$;

Alternatively, W and Z taken together with the carbon to which they are attached to form an olefin, or substituted olefin, an epoxide, a carbonyl, substituted or unsubstituted heterocyclic ring, or a C3-C7 carbocyclic, carbonate, or carbamate;

Each of X and Y is independently:
a) hydrogen;
b) halogen; or
c) —R$_2$;

Each of R$_8$ and R$_9$ is independently selected from the group R$_2$; or R$_8$ and R$_9$ can be taken together with the nitrogen atom to which they are attached to form a substituted or unsubstituted heterocyclic ring;

R$_p$ is hydrogen, hydroxyl protecting group or hydroxyl prodrug group.

2. A compound of claim 1 represented by the formula (II):

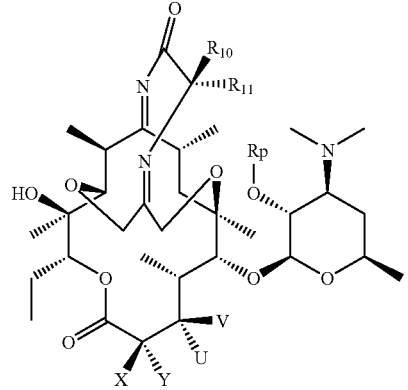

(II)

Each of R$_{10}$ and R$_{11}$ is independently:
a) hydrogen;
b) deuterium;
c) halogen;
d) —R$_2$;
e) —COR$_2$;
f) —SO$_2$R$_2$; or
g) alternatively, can be taken together with the carbon atom to which they are attached are selected from the group consisting of: C=O and C=CHR$_2$.

3. A compound of claim 2 represented by the formula (III):

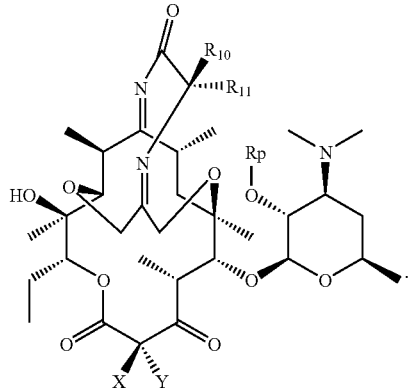

(III)

4. A compound of claim 1 represented by the formula (IV):

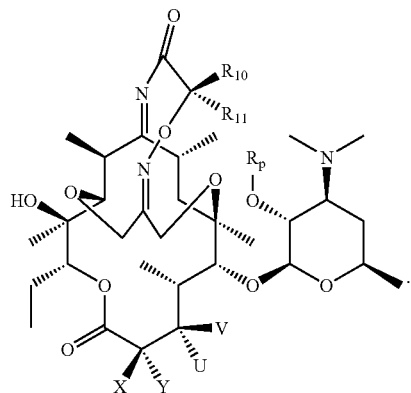

5. A compound of claim 4 represented by the formula (V):

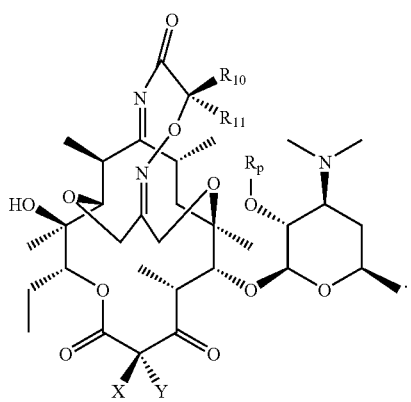

6. A compound according to claim 4 selected from the group consisting of:
   (1) Compound of formula (IV), wherein V, Y, $R_{10}$ and $R_{11}$ are hydrogen, X is methyl, $R_p$=Ac, and U is hydroxyl;
   (2) Compound of formula (IV), wherein V, Y, and $R_{11}$ are hydrogen, $R_{10}$=Ph, X is methyl, $R_p$=Ac, and U is hydroxyl;
   (3) Compound of formula (IV), wherein V, Y, and $R_{11}$ are hydrogen, $R_{10}$=Bn, X is methyl, $R_p$=Ac, and U is hydroxyl;
   (4) Compound of formula (IV), wherein V, Y, and $R_{10}$ are hydrogen, $R_{11}$=Bn, X is methyl, $R_p$=Ac, and U is hydroxyl; and
   (5) Compound of formula (IV), wherein V, Y, and $R_{11}$ are hydrogen, $R_{10}$=CH$_2$CH$_2$Ph, X is methyl, $R_p$=Ac, and U is hydroxyl.

7. A compound of claim 1 having the formula (A), selected from the compounds (11)-(107) delineated in Table 1:

TABLE 1

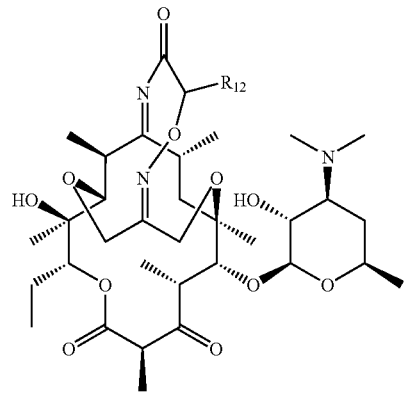

| Compound | $R_{12}$ |
|---|---|
| (11) | 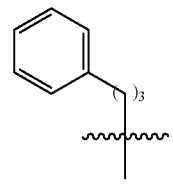 |
| (12) | 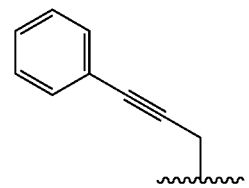 |
| (13) | 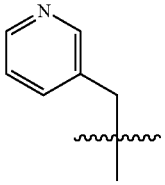 |
| (14) | 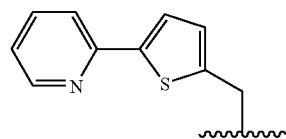 |
| (15) | 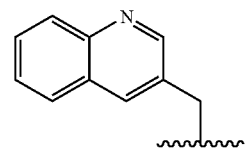 |
| (16) | 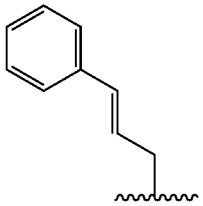 |

TABLE 1-continued
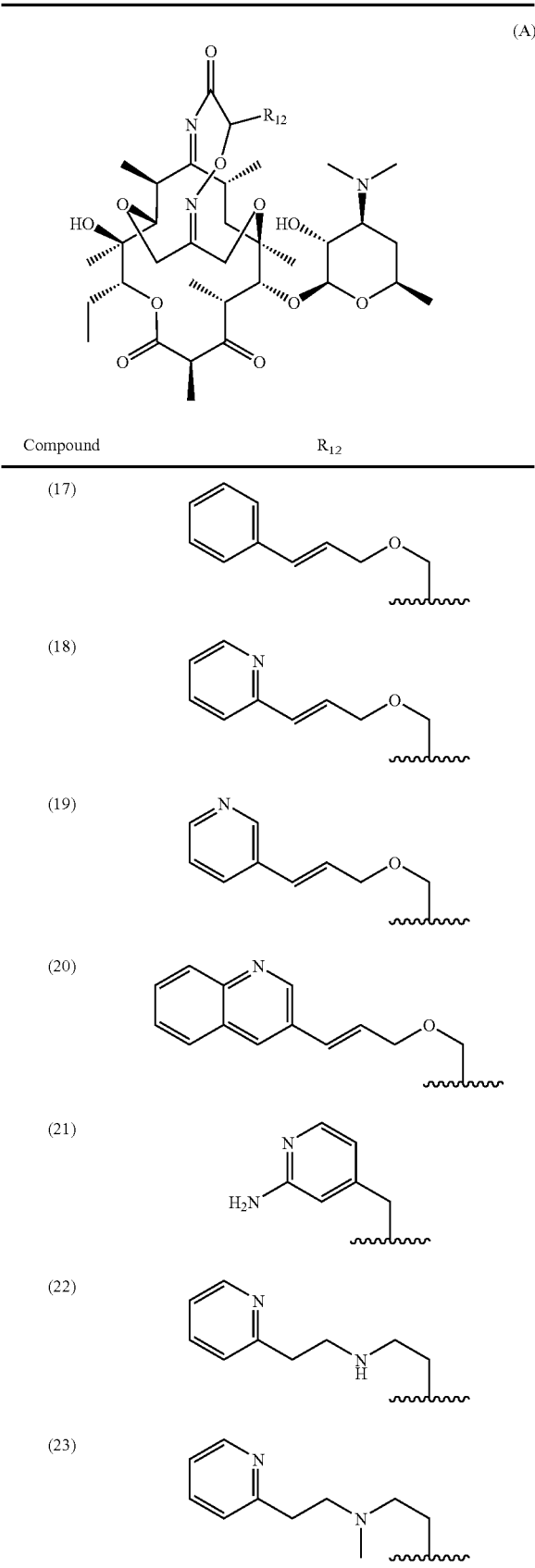
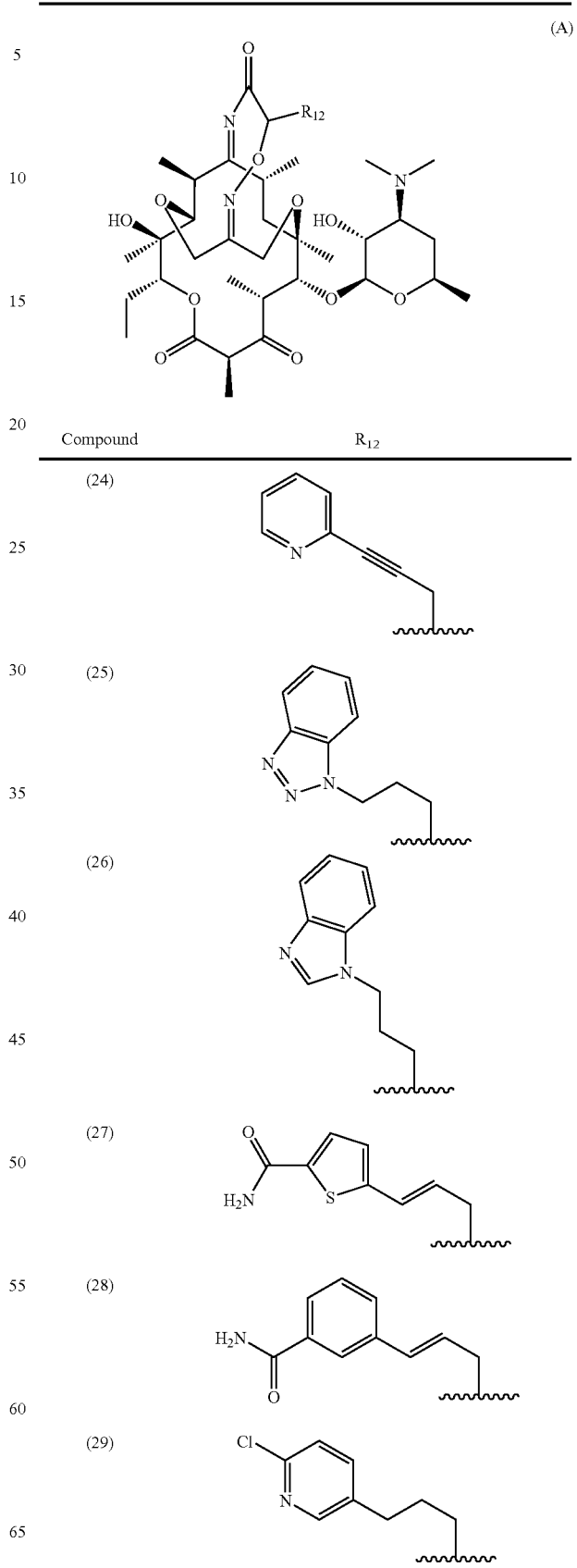

TABLE 1-continued
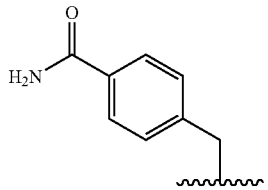
(A)
| Compound | R₁₂ |
|---|---|
| (30) | 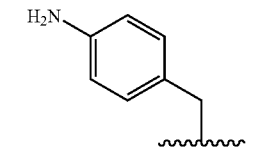 |
| (31) | 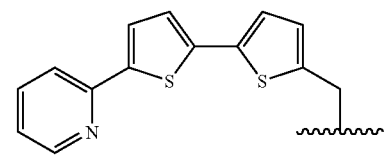 |
| (32) | 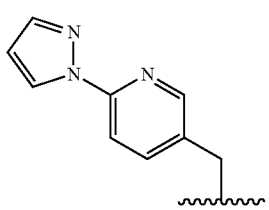 |
| (33) | 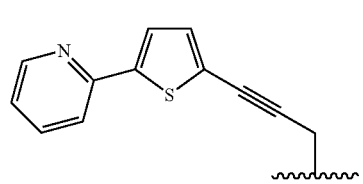 |
| (34) | 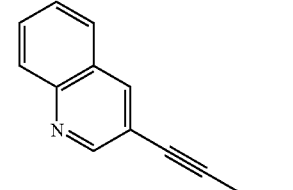 |
| (35) | 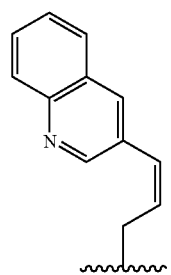 |
TABLE 1-continued
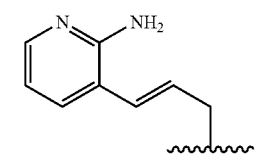
(A)
| Compound | R₁₂ |
|---|---|
| (36) | 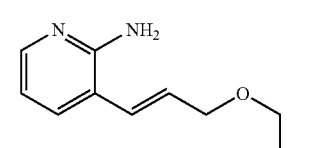 |
| (37) | 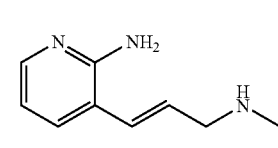 |
| (38) | 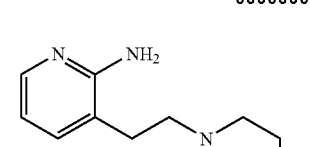 |
| (39) | 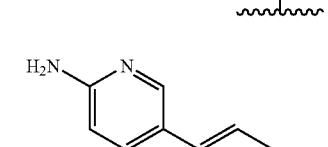 |
| (40) | |
| (41) | |

TABLE 1-continued
(A)
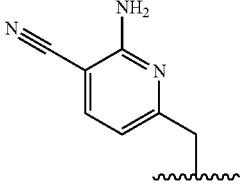
| Compound | R$_{12}$ |
|---|---|
| (42) | 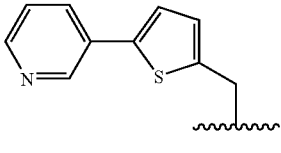 |
| (43) | 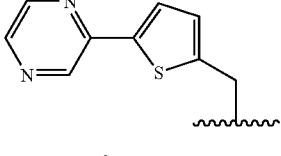 |
| (44) | 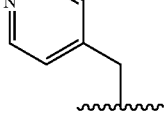 |
| (45) | 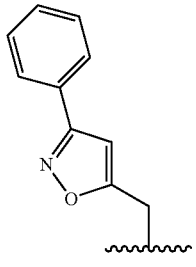 |
| (46) | 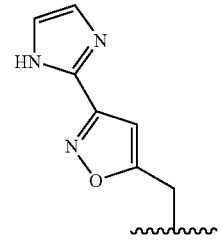 |
| (47) | 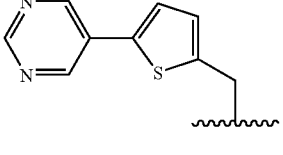 |
TABLE 1-continued
(A)
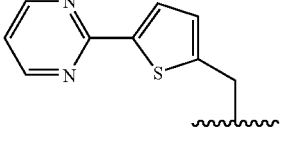
| Compound | R$_{12}$ |
|---|---|
| (48) | 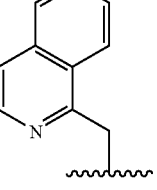 |
| (49) | 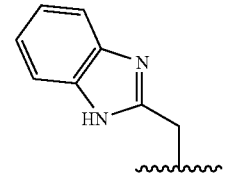 |
| (50) | 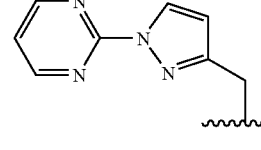 |
| (51) | 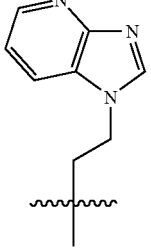 |
| (52) | |
| (53) | |

TABLE 1-continued (A)

| Compound | R₁₂ |
|---|---|
| (54) | 3-(purin-9-yl)butyl |
| (55) | (1-benzyl-1H-imidazol-2-yl)methyl |
| (56) | 1-(5-(pyridin-2-yl)thiophen-2-yl)ethyl |
| (57) | (5-(thiophen-2-yl)-1,2,4-oxadiazol-3-yl)methyl |
| (58) | (5-carbamoylthiophen-2-yl)methyl |
| (59) | (3-(pyridin-2-yl)thiophen-2-yl)methyl |

TABLE 1-continued (A)

| Compound | R₁₂ |
|---|---|
| (60) | (5-(pyridin-2-ylcarbamoyl)thiophen-2-yl)methyl |
| (61) | (5-(benzylcarbamoyl)thiophen-2-yl)methyl |
| (62) | (4-carbamoylphenyl)methyl |
| (63) | 2-(pyridin-2-ylcarbamoyl)ethyl |
| (64) | (5-(phenylcarbamoyl)thiophen-2-yl)methyl |
| (65) | (4-(phenylcarbamoyl)phenyl)methyl |

TABLE 1-continued
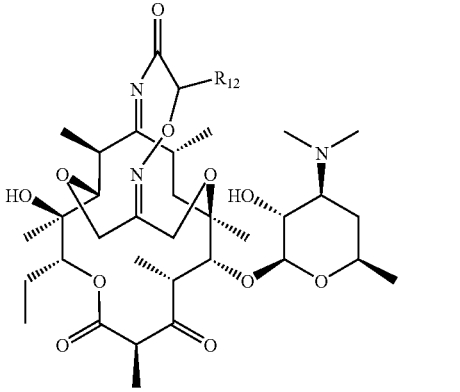
(A)
| Compound | R$_{12}$ |
|---|---|
| (66) | 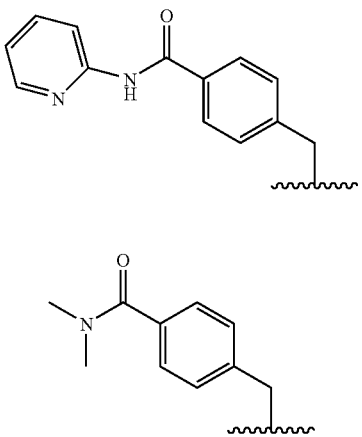 |
| (67) | 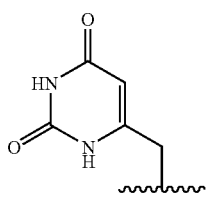 |
| (68) | 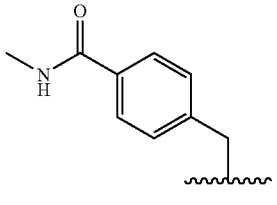 |
| (69) | 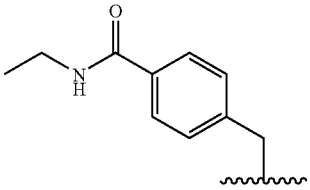 |
| (70) | 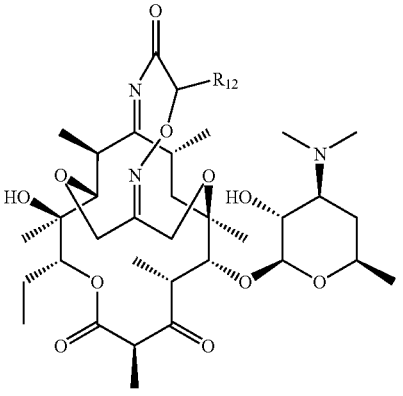 |
TABLE 1-continued
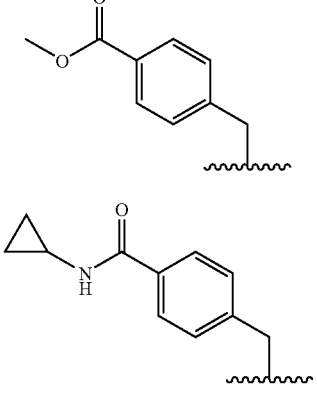
(A)
| Compound | R$_{12}$ |
|---|---|
| (71) | 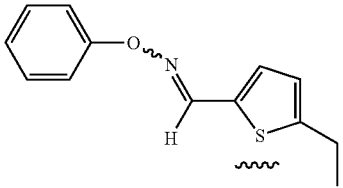 |
| (72) | 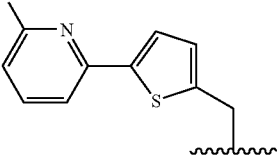 |
| (73) | 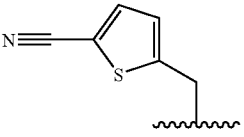 |
| (74) | 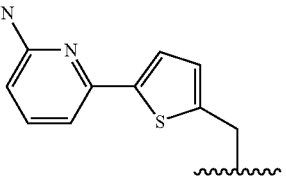 |
| (75) | |
| (76) | |

TABLE 1-continued (A)

| Compound | R₁₂ |
|---|---|
| (77) | 6-cyanopyridin-2-yl-isoxazol-5-yl-methylene |
| (78) | 5-(thiophen-2-yl)pyridin-2-yl-methylene |
| (79) | 5-(pyrazin-2-yl)pyridin-2-yl-methylene |
| (80) | 6-cyano-2-(thiophen-2-yl)pyridine |
| (81) | 5-(pyridin-2-yl)pyridin-2-yl-methylene |
| (82) | 6-amino-2,3'-bipyridine |
| (83) | 6-carboxamidopyridin-2-yl-isoxazol-5-yl-methylene |
| (84) | 6-aminopyridin-3-yl-butylene |
| (85) | 6-cyanopyridin-3-yl-methylene |
| (86) | 5-cyanothiophen-2-yl-isoxazol-3-yl-methylene |

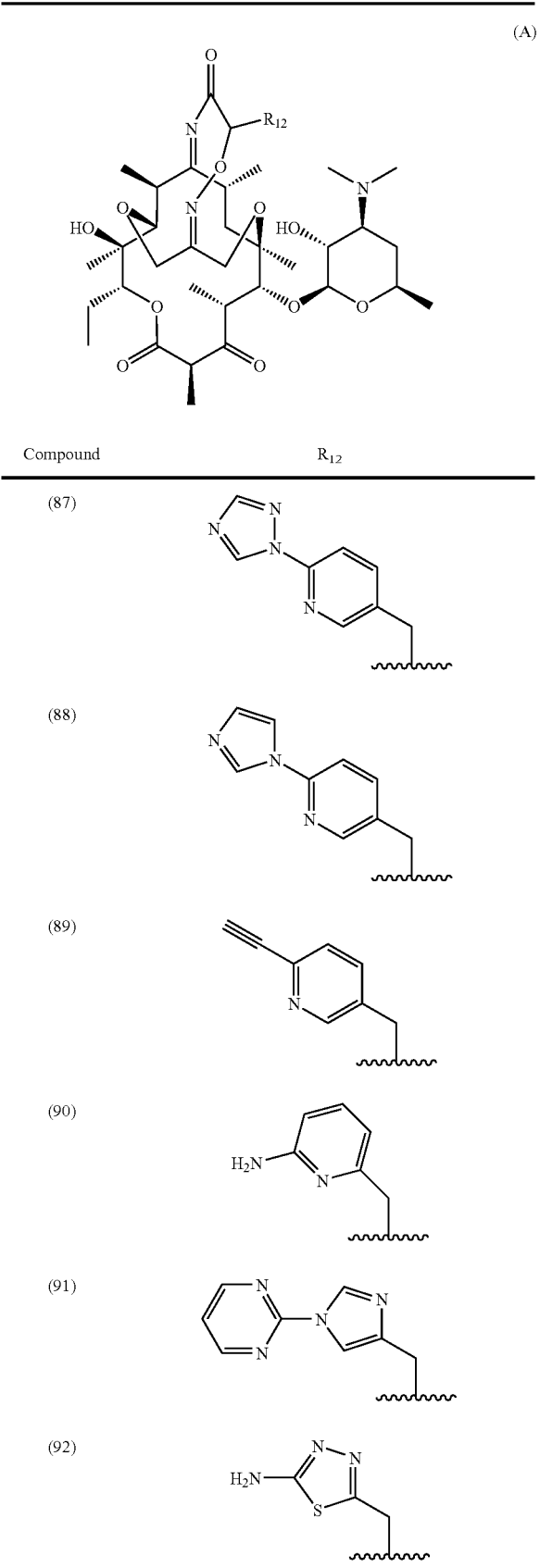
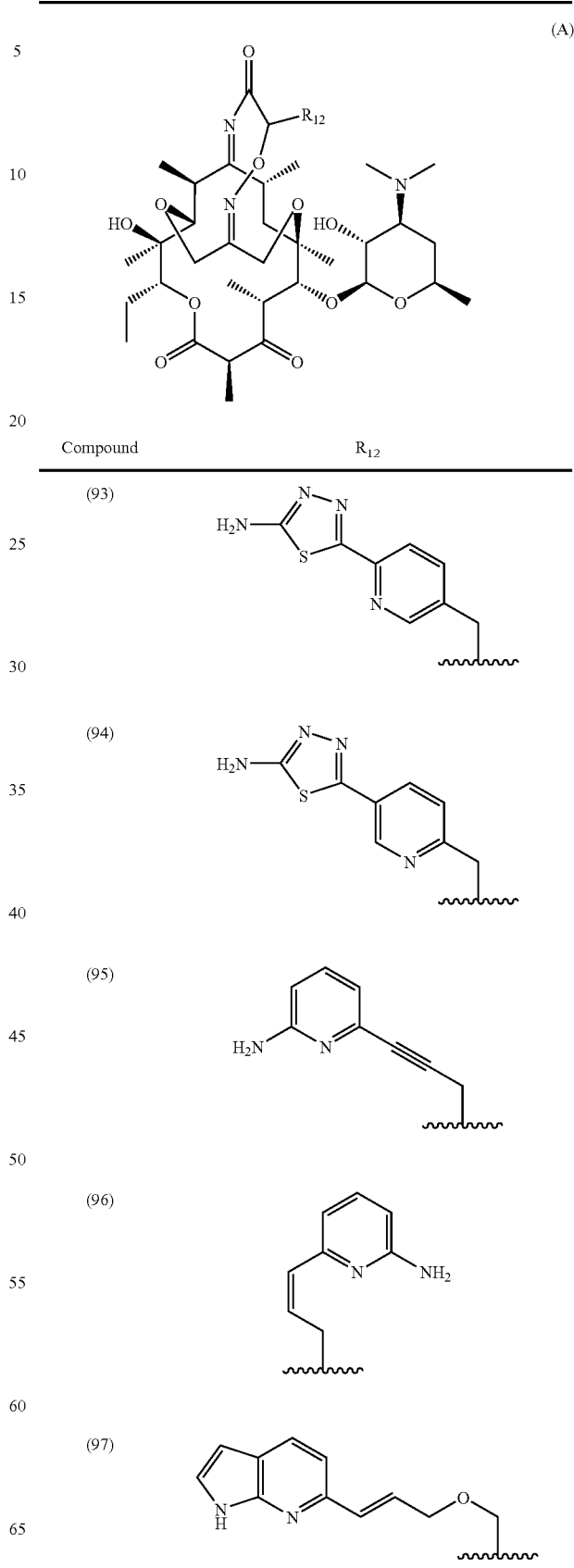

TABLE 1-continued

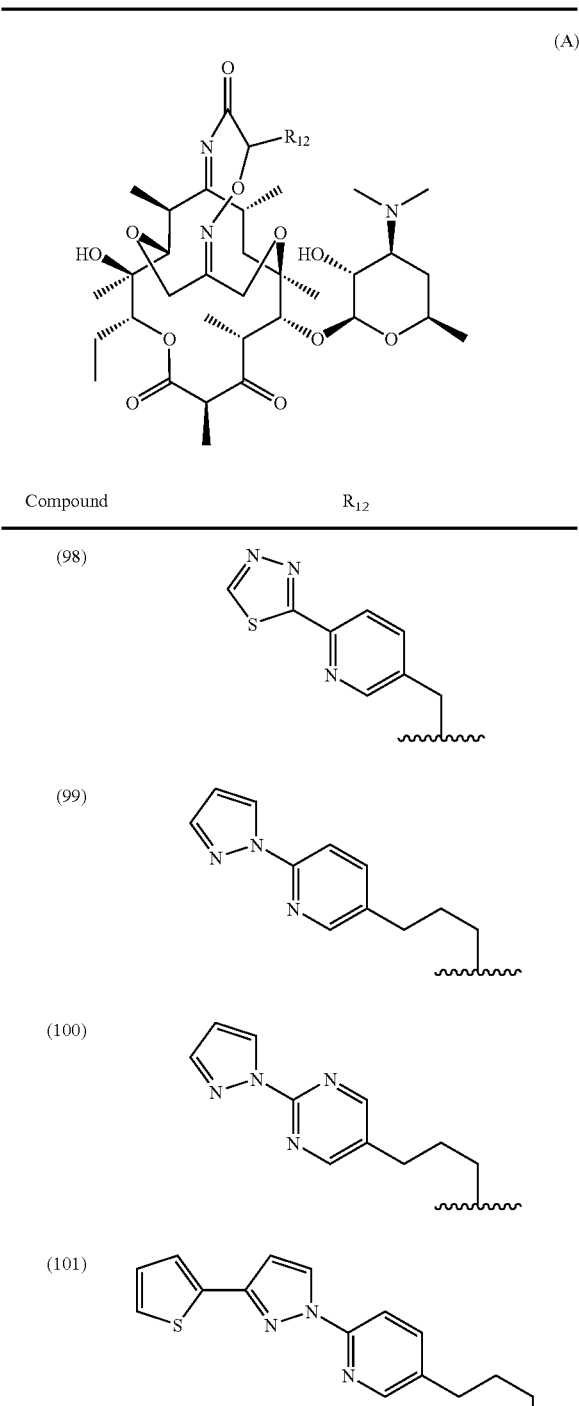

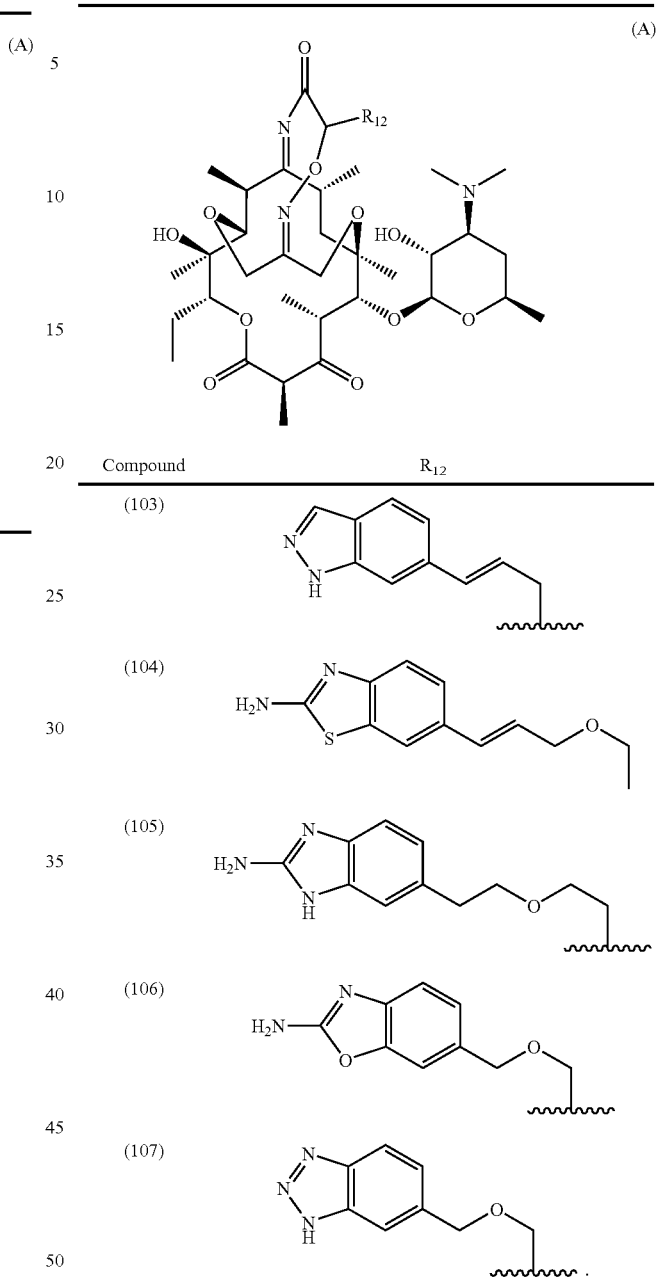

8. A pharmaceutical composition comprising a therapeutically effective amount of a compound of claim 1 or a pharmaceutically acceptable salt, ester or prodrug thereof, in combination with a pharmaceutically acceptable carrier.

9. A method for treating a bacterial infection in a subject, comprising administering to said subject a therapeutically effective amount of a pharmaceutical composition of claim 8.

10. A method of treating cystic fibrosis in a patient, comprising administering to said subject, a therapeutically effective amount of a pharmaceutical composition of claim 8.

11. A method of treating inflammation in a subject comprising administering to said subject, a therapeutically effective amount of pharmaceutical composition of claim 8.

12. A process for preparing a compound according to claim 1 represented by the formula:

(a) reacting a compound represented by the formula:

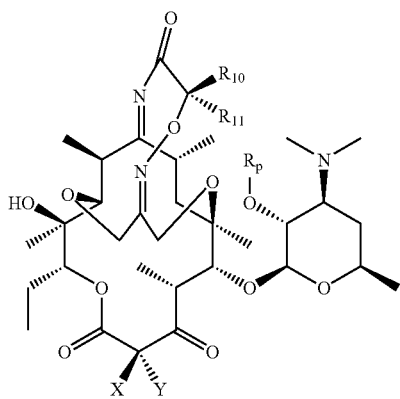
(V)

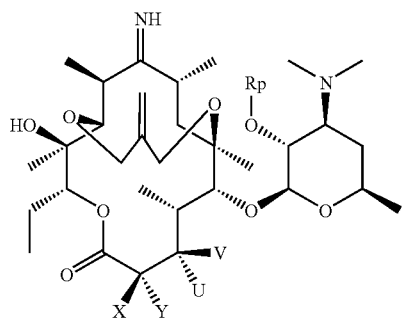

with a carboxylic acid derivative in the presence of a coupling reagent to provide a compound represented by the formula (VI)

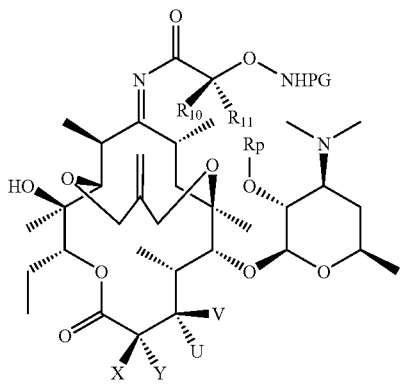
(VI)

(b) reacting a compound of formula (VI) from step (a) with a reagent or reagents capable of performing oxidative cleavage to provide a compound represented by the formula (VII)

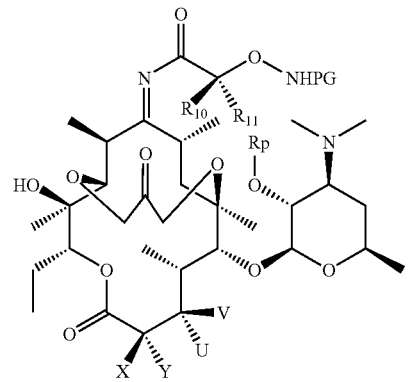
(VII)

(c) reacting a compound of formula (VII) from step (b) with a deprotecting reagent to remove a protective group from the nitrogen in the presence of an acid to provide a compound represented by formula (IV):

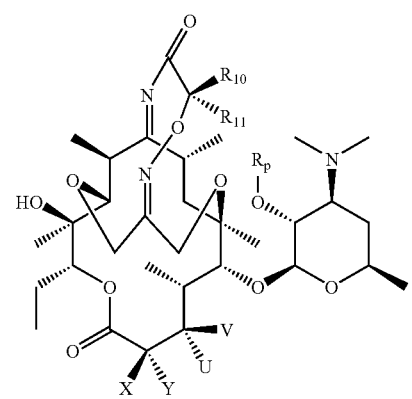
(IV)

(d) optionally when V is hydrogen and U is a hydroxy, reacting a compound of formula (IV) from step (c) with an oxidizing agent to provide a compound represented by formula (V):

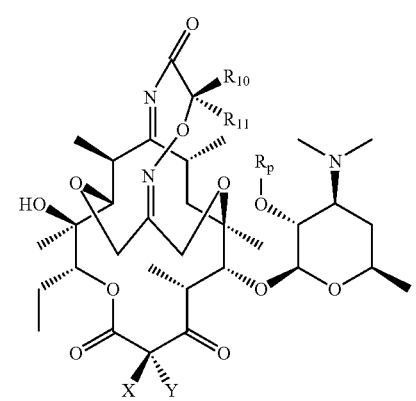
(V)

(e) optionally deprotecting the compound formed in step (c).

13. A compound according to claim 5 selected from the group consisting of:
(1) Compound of formula (V), wherein Y, $R_{10}$ and $R_{11}$ are hydrogen, X is methyl, and $R_p$=H;
(2) Compound of formula (V), wherein Y, and $R_{11}$ are hydrogen, $R_{10}$=Ph, X is methyl, and $R_p$=H;
(3) Compound of formula (V), wherein Y, and $R_{11}$ are hydrogen, $R_{10}$=Bn, X is methyl, and $R_p$=H;
(4) Compound of formula (V), wherein Y, and $R_{10}$ are hydrogen, $R_{11}$=Bn, X is methyl, and $R_p$=H; and
(5) Compound of formula (V), wherein Y, and $R_{11}$ are hydrogen, $R_{10}$=$CH_2CH_2Ph$, X is methyl, and $R_p$=H.

* * * * *

UNITED STATES PATENT AND TRADEMARK OFFICE
CERTIFICATE OF CORRECTION

PATENT NO. : 7,589,067 B2
APPLICATION NO. : 11/545241
DATED : September 15, 2009
INVENTOR(S) : Yat Sun Or et al.

Page 1 of 1

It is certified that error appears in the above-identified patent and that said Letters Patent is hereby corrected as shown below:

Column 58

At line 38, delete "–J–" and replace with -- –J-$R_1$– --; and

At line 49, delete "–C1-$_{C6}$" and replace with -- –$C_1$-$C_6$ --.

Signed and Sealed this

Fifth Day of January, 2010

David J. Kappos
*Director of the United States Patent and Trademark Office*